(12) United States Patent
Garrett

(10) Patent No.: US 9,511,034 B1
(45) Date of Patent: *Dec. 6, 2016

(54) METHOD FOR APPLYING A SKIN TREATMENT

(71) Applicant: Beauty Blend, Inc., Laguna Beach, CA (US)

(72) Inventor: Shien-lin Garrett, Laguna Beach, CA (US)

(73) Assignee: Bio-Silicote, Inc., Laguna Beach, CA (US)

( * ) Notice: Subject to any disclaimer, the term of this patent is extended or adjusted under 35 U.S.C. 154(b) by 73 days.

This patent is subject to a terminal disclaimer.

(21) Appl. No.: 14/337,098

(22) Filed: Jul. 21, 2014

Related U.S. Application Data

(60) Provisional application No. 61/913,821, filed on Dec. 9, 2013.

(51) Int. Cl.
*A61K 9/70* (2006.01)
*A61K 8/89* (2006.01)
*A61Q 19/08* (2006.01)

(52) U.S. Cl.
CPC .............. *A61K 9/7015* (2013.01); *A61K 8/89* (2013.01); *A61Q 19/08* (2013.01); *A61K 2800/95* (2013.01)

(58) Field of Classification Search
CPC .... A61K 9/7015; A61K 8/89; A61K 2800/95; A61Q 19/08
See application file for complete search history.

(56) References Cited

U.S. PATENT DOCUMENTS

| | | | |
|---|---|---|---|
| 3,908,018 A | 9/1975 | Choay | |
| 4,694,021 A | 9/1987 | Schweiger | |
| 5,360,851 A | 11/1994 | Feder et al. | |
| 5,789,445 A | 8/1998 | Schweiger | |
| 5,885,581 A | 3/1999 | Massand | |
| 6,521,271 B1 | 2/2003 | Phan | |
| 6,572,878 B1 | 6/2003 | Blain2 | |
| 6,579,543 B1 * | 6/2003 | McClung | A61K 8/345 424/401 |
| 6,827,929 B1 | 12/2004 | Lord et al. | |
| 7,241,451 B1 | 7/2007 | Edell et al. | |
| 8,021,683 B2 | 9/2011 | Berlat | |
| 8,399,002 B2 | 3/2013 | Chrysopoulo et al. | |
| 8,409,600 B2 | 4/2013 | Friedman et al. | |
| 8,518,879 B2 | 8/2013 | Al-Qahtani | |
| 8,563,604 B2 | 10/2013 | Palefsky et al. | |
| 8,691,202 B2 | 4/2014 | Yu et al. | |
| 9,333,223 B2 | 5/2016 | Yu et al. | |
| 2005/0143345 A1 | 6/2005 | Hardy | |
| 2005/0191328 A1 | 9/2005 | Taniguchi | |
| 2007/0269537 A1 | 11/2007 | Gupta | |
| 2008/0226577 A1 * | 9/2008 | L'Alloret | A61K 8/8158 424/70.12 |
| 2008/0241230 A1 | 10/2008 | Matloub et al. | |
| 2009/0143333 A1 | 6/2009 | Palefsky et al. | |
| 2010/0196454 A1 | 8/2010 | Keller | |
| 2011/0046532 A1 | 2/2011 | Kaila et al. | |
| 2012/0121721 A1 | 5/2012 | James | |
| 2012/0192886 A1 | 8/2012 | Singer | |
| 2012/0219514 A1 | 8/2012 | Bonnichsen | |
| 2012/0276226 A1 | 11/2012 | Anthonavage et al. | |
| 2013/0165420 A1 | 6/2013 | Ray, II et al. | |
| 2014/0356436 A1 * | 12/2014 | Mouzin | A61Q 19/08 424/489 |

FOREIGN PATENT DOCUMENTS

| | | |
|---|---|---|
| EP | 0923937 A2 | 6/1999 |
| EP | WO0122923 A2 | 4/2001 |
| EP | 1467702 A1 | 10/2004 |
| EP | 2258406 A2 | 12/2010 |
| EP | 2412368 A1 | 2/2012 |
| EP | 2258406 A3 | 5/2012 |
| GB | WO0123011 A1 | 4/2001 |
| GB | WO03051326 A1 | 6/2003 |
| GB | WO2004105821 A1 | 12/2004 |
| IL | WO2009031153 A2 | 3/2009 |
| WO | WO 88/00039 * | 1/1988 |
| WO | WO2010148310 A1 | 12/2010 |
| WO | WO2011085278 A2 | 7/2011 |
| WO | WO2013101929 A1 | 7/2013 |

OTHER PUBLICATIONS

Elmer's Stix-All (attp://www.wsc.edu/facility_services/msds/stix_all.pdf> available Sep. 29, 2008, provided in Form 1449 filed Feb. 16, 2016).*
http://www.lorealparisusa.com/en/products/makeup/face/face-powder/infallible-pro-matte-powder.aspx.*

(Continued)

*Primary Examiner* — Blessing M Fubara
(74) *Attorney, Agent, or Firm* — Fish & Tsang, LLP

(57) ABSTRACT

The invention is generally a skin treatment for managing skin conditions ranging from scars, including keloids, to burns and wrinkles. The skin treatment may comprise of several components including a cleansing solution, a silicone elastomer, and a mineral powder that may be utilized to treat and camouflage the affected skin. In one embodiment, a cleansing component is used to prime a skin area, cleansing and treating the area so that a silicone component can heal the skin.

16 Claims, 8 Drawing Sheets

(56) References Cited

OTHER PUBLICATIONS

"Silicone for Scars," unknown publishing date, unknown publisher, accessed Nov. 2013, <http://www.siliconeforscars.com>.
Michelle Alford, "Growing Up Scarred: Burn Scars and Children," Scars1.corn, Nov. 8 2010, accessed Nov. 2013, < htip://scars1.com/news/Growing_Up_Scarred_Burn_Scars_and_Children>.
"Keloid Removal—Research Into Silicone Based Keloid Scar Removal," Oct. 22, 2012, Tinnitus Treatment Blog, accessed Nov. 2013, www.suportelivre.org/keloid-removal-research-into-silicone-based-keloid-scar-removal-products>.
ScarAway®—Clinical Studies, Enaltus, LLC, unknown publishing date, accessed Nov. 2013, <http://www.myscaraway.com/clinical-studies/index.html>.
Neerja Puri and Ashutosh Talwar, "The Efficacy of Silicone Gel for the Treatment of Hypertrophic Scars and Keloids," Medknow Publications, Jul. 2009, accessed Nov. 2013, <http://www.ncbi.nlm.nih.gov/pmc/articles/PMC2918339/.
Cathryn Delude, "Do scar remedies really work'?" Los Angeles Times, Apr. 17, 2011, accessed Nov. 2013, < http://articles.latimes.com/2011/apr/17/health/la-he-scars-20110417>.
Michelle Alford, "Growing Up Scarred: Burn Scars and Children," Scars1.com, Nov. 8 2010, accessed Nov. 2013, < http://scars1.com/news/Growing_Up_Scarred_Burn_Scars_and_Children>.
Neerja Puri and Ashutosh Talwar, "The Efficacy of Silicone Gel for the Treatment of Hypertrophic Scars and Keloids," Medknow Publications, Jul. 2009, accessed Nov. 2013, <http://www.ncbi.nlm.nih.gov/pmc/articles/PMC2918339/>.
Cathryn Delude, "Do scar remedies really work?" Los Angeles Times, Apr. 17, 2011, accessed Nov. 2013, <htttp://articles.latimes.com/2011/apr/17/health/la-he-scars-20110417>.
Elmer's Stix-All (<http://www.wsc.edu/facility_services/msds/stix_all.pdf> available Sep. 29, 2008, accessed Mar. 10, 2015).

\* cited by examiner

METHOD FOR APPLYING A SKIN TREATMENT

PRIORITY NOTICE

The present application claims priority under 35 U.S.C. §119(e) to the U.S. Provisional Patent Application with Ser. No. 61/913,821 filed on Dec. 9, 2013, the disclosure of which is incorporated herein by reference in its entirety.

TECHNICAL FIELD OF THE INVENTION

The present invention relates to a skin treatment and camouflage composition, and more particularly, to one or more compositions including a solution, silicone elastomer, and mineral powder that may be utilized to treat and camouflage skin conditions such as scars and wrinkles, including methods of preparation, methods of use, and devices for storing and dispensing the skin treatment.

COPYRIGHT AND TRADEMARK NOTICE

A portion of the disclosure of this patent application may contain material that is subject to copyright protection. The owner has no objection to the facsimile reproduction by anyone of the patent document or the patent disclosure, as it appears in the Patent and Trademark Office patent file or records, but otherwise reserves all copyrights whatsoever.

Certain marks referenced herein may be common law or registered trademarks of third parties affiliated or unaffiliated with the applicant or the assignee. Use of these marks is by way of example and should not be construed as descriptive or to limit the scope of this invention to material associated only with such marks.

BACKGROUND OF THE INVENTION

Regardless of scar source or type, almost every person has or will have one or more cosmetically undesirable scars of some magnitude on their face or body. It is well known that scarring generates negative emotional problems, damaging confidence and self-esteem. Additionally, depending on scar severity and location, the scar itself may create functional problems for the person, such as restricting movement around the location of the scar or making certain garments unwearable. Similarly, although perhaps not as emotionally and physically challenging, wrinkles often present a similar problem in that for various reasons they become undesirable features of a person's skin.

Unfortunately, treatment and camouflaging of skin, whether for scars or wrinkles, are frequently treated as separate issues. Thus, attempts to treat skin are often ill-suited for camouflaging skin and vice versa. To illustrate, camouflaging of scars aids in mitigating some of the self-esteem issues associated with having such scars. However, scar camouflaging products frequently require application one or more times a day and have a negligible impact on the actual condition of the scar. Thus, the scar is merely masked, not treated. Similarly, wrinkles are often camouflaged with make-up, but typically not treated to adequately alleviate the condition.

Conversely, treatment of scars, or wrinkles, generally requires repeated courses of a given treatment, wherein the given treatment course may last days, weeks, months, or even years. During this often lengthy treatment regimen, the need to camouflage the skin still exists, yet this need is inadequately met by the prior art. Furthermore, known skin treatments require daily or almost daily application, which results in diminished user compliance.

Therefore, there is a strong need in the art for a synergistic skin treatment that addresses both the healing and cosmetic aspects of skin management, which minimizes the curing times and the frequency of required use for such management, in order to encourage higher user compliance rates. It is to these ends that the present invention has been developed.

BRIEF SUMMARY OF THE INVENTION

To minimize the limitations in the prior art, and to minimize other limitations that will be apparent upon reading and understanding the present specification, the present specification describes a skin treatment including a cleansing solution, silicone elastomer, and mineral powder that may be utilized together to treat and camouflage skin affected by scars, burns, or undesirable wrinkles. Furthermore, methods of preparation, methods of use and a device for storing and dispensing the skin treatment are also described.

A skin treatment composition, in accordance with one embodiment of the present invention, comprises: a solution for forming a first layer over damaged skin, the solution comprising: isopropyl alcohol, colloidal silver, chamomile extract, and gotu kola extract; a silicone mixture for forming a second layer over the first layer, the silicone mixture comprising: polydimethylsiloxane, noncrystalline silicone dioxide, a methylhydride crosslinker, a platinum catalyst, and hydroxyl terminated polymethylphenylsiloxane; and a mineral powder for forming a third layer over the second layer, the mineral powder comprising: mica and a natural mineral kaolinite.

Another skin treatment composition, in accordance with one embodiment of the present invention, comprises: a first silicone elastomer including: 50-80% by wt. of a polydimethylsiloxane, 10-25% by wt. of a noncrystalline silicone dioxide, 0.03-0.09% by wt. of a platinum catalyst, and 0.18-0.49% by wt. of a hydroxyl terminated polymethylphenylsiloxane; and a second silicone elastomer including: 50-80% by wt. of a polydimethylsiloxane, 10-25% by wt. of a noncrystalline silicone dioxide, no more than 10% by wt. of a methylhydride crosslinker, and 0.18-0.49% by wt. of a hydroxyl terminated polymethylphenylsiloxane, wherein the first and second silicone elastomers are configured to react when mixed in order to form a film layer for treating a skin area.

A kit for providing a skin treatment, in accordance with one embodiment of the present invention, comprises: a first container including: a first compartment configured to hold a first silicone elastomer, the first silicone elastomer comprising: 50-80% by wt. of a polydimethylsiloxane, 10-25% by wt. of a noncrystalline silicone dioxide, 0.03-0.09% by wt. of a platinum catalyst, and 0.18-0.49% by wt. of a hydroxyl terminated polymethylphenylsiloxane; and a second compartment configured to hold a second silicone elastomer, the second silicone elastomer comprising: 50-80% by wt. of a polydimethylsiloxane, 10-25% by wt. of a noncrystalline silicone dioxide, no more than 10% by wt. of a methylhydride crosslinker, and 0.18-0.49% by wt. of a hydroxyl terminated polymethylphenylsiloxane; a second container including a solution, the solution comprising: 0.5-3% by wt. of an isopropyl alcohol, 73-90% by wt. of a colloidal silver, 1-5% by wt. of a chamomile extract, and 1-5% by wt. of a gotu kola extract; and a third container including a mineral powder, the mineral powder comprising: 3-5% by wt. of a natural mineral kaolinite, and 61-63% by wt. of mica.

A container for storing a skin treatment composition, in accordance with one embodiment of the present invention, comprises: a first compartment that holds a solution, the solution including: 0.5-3% by wt. of an isopropyl alcohol, 73-90% by wt. of a colloidal silver, 1-5% by wt. of a chamomile extract, and 1-5% by wt. of a gotu kola extract; a second compartment including a first chamber and a second chamber, wherein: the first chamber holds a first silicone elastomer, the first silicone elastomer including: 50-80% by wt. of a polydimethylsiloxane, 10-25% by wt. of a noncrystalline silicone dioxide, 0.03-0.09% by wt. of a platinum catalyst, and 0.18-0.49% by wt. of a hydroxyl terminated polymethylphenylsiloxane; and the second chamber holds a second silicone elastomer, the second silicone elastomer comprising: 50-80% by wt. of a polydimethylsiloxane, 10-25% by wt. of a noncrystalline silicone dioxide, no more than 10% by wt. of a methylhydride crosslinker, and 0.18-0.49% by wt. of a hydroxyl terminated polymethylphenylsiloxane; and a third compartment including a mineral powder, the mineral powder including 3-5% by wt. of a natural mineral kaolinite.

A method for preparing a skin treatment, in accordance with one embodiment of the present invention, comprises: preparing a first mixture by combining a silicone platinum catalyst with a first volume of a silicone elastomer, wherein the first mixture includes between 0.03% to 0.09% by wt. of the silicone platinum catalyst; and preparing a second mixture by combining amorphous fumed silica to a second volume of the silicone elastomer, wherein the second mixture includes between 0.49% to 0.98% by wt. of the amorphous fumed silica.

Another method for preparing a skin treatment, in accordance with one embodiment of the present invention, comprises: preparing a first mixture by combining a silicone platinum catalyst with a first volume of a silicone elastomer, wherein the silicone platinum catalyst is added to the first volume of the silicone elastomer in the proportion of 1 to 2 grams of the silicone platinum catalyst per kilogram of the first volume of the silicone elastomer; and preparing a second mixture by: (i) combining amorphous fumed silica and *Boswellia serrata* extract with a second volume of the silicone elastomer, wherein the amorphous fumed silica is added to the second volume of the silicone elastomer so the resulting concentration of amorphous fumed silica is 0.0015 g/mL, wherein the *Boswellia serrata* extract is added to the second volume of the silicone elastomer so the resulting concentration of *Boswellia serrata* extract is 0.005 g/mL, and wherein the second volume of the silicone elastomer and the first volume of the silicone elastomer have equal volumes; (ii) heating the resulting mixture of step (i) to a range of 75 to 90 degrees Celsius, while mixing; (iii) cooling the resulting mixture of step (ii) to room temperature; (iv) combining, to the resulting mixture of step (iii), gotu kola extract, chamomile extract, green tea extract, and tetrahydrocurcumoid.

Yet another method for preparing a scar treatment, in accordance with one embodiment of the present invention, comprises: (1) preparing a solution for cleansing skin by mixing: 5-3% by wt. of an isopropyl alcohol, 73-90% by wt. of a colloidal silver, 1-5% by wt. of a chamomile extract, and 1-5% by wt. of a gotu kola extract, 1-5% by wt. of a green tea extract, 1-4% by wt. of a tetrahydroidcurcuminoid, and 1-5% by wt. of a *Boswellia serrata* extract; (2) preparing a silicone composition for applying to skin that has been treated with the solution by: (i) preparing a first mixture by combining a silicone platinum catalyst with a first volume of a silicone elastomer, wherein the first mixture includes between 0.03% to 0.09% by wt. of the silicone platinum catalyst; combining amorphous fumed silica to the first mixture, wherein the first mixture includes between 0.49% to 0.98% by wt. of the amorphous fumed silica; combining cyclopentasiloxane with the first mixture, wherein the first mixture includes between 0.25-0.49% by wt. of the cyclopentasiloxane; combining hydroxyl terminated polymethylphenylsiloxane with the first mixture, wherein the first mixture includes between 0.18-0.49% by wt. of the hydroxyl terminated polymethylphenylsiloxane; combining dimethicone with the first mixture, wherein the first mixture includes between 0.49-0.98% by wt. of dimethicone; (ii) preparing a second mixture by: combining amorphous fumed silica to a second volume of the silicone elastomer, wherein the second mixture includes between 0.49% to 0.98% by wt. of the amorphous fumed silica; combining cyclopentasiloxane with the second mixture, wherein the second mixture includes between 0.25-0.49% by wt. of the cyclopentasiloxane; combining hydroxyl terminated polymethylphenylsiloxane with the second mixture, wherein the second mixture includes between 0.18-0.49% by wt. of the hydroxyl terminated polymethylphenylsiloxane; combining dimethicone with the second mixture, wherein the second mixture includes between 0.49-0.98% by wt. of dimethicone; wherein the first volume of the silicone elastomer and the second volume of the silicone elastomer are equal volumes; (3) degassing the first and second mixtures for a period of at least five to twenty minutes; and (4) storing the solution, the first mixture and the second mixture in separate vessels for at least a 24 hour period.

A method for treating skin, in accordance with one embodiment of the present invention, comprises: (1) applying a first solution to a skin area, wherein the first solution comprises: 0.5-3% by wt. of an isopropyl alcohol, 73-90% by wt. of a colloidal silver, 1-5% by wt. of a chamomile extract, and 1-5% by wt. of a gotu kola extract; (2) applying a second solution on the skin area treated with the first solution, the second solution including a silicone elastomer, wherein the silicone elastomer comprises: 50-80% by wt. of a polydimethylsiloxane, 10-25% by wt. of a noncrystalline silicone dioxide, no more than 10% by wt. of a methylhydride crosslinker, 0.015-0.045% by wt. of a platinum catalyst, and 0.18-0.49% by wt. of a hydroxyl terminated polymethylphenylsiloxane; and (3) curing the silicone elastomer for a predetermined period of time.

Another method for treating skin, in accordance with one embodiment of the present invention, comprises: (1) providing a first silicone elastomer including: 50-80% by wt. of a polydimethylsiloxane, 10-25% by wt. of a noncrystalline silicone dioxide, no more than 10% by wt. of a methylhydride crosslinker, 0.03-0.09% by wt. of a platinum catalyst, and 0.18-0.49% by wt. of a hydroxyl terminated polymethylphenylsiloxane; (2) providing a second silicone elastomer including: 50-80% by wt. of a polydimethylsiloxane, 10-25% by wt. of a noncrystalline silicone dioxide, no more than 10% by wt. of a methylhydride crosslinker, and 0.18-0.49% by wt. of a hydroxyl terminated polymethylphenylsiloxane; (3) creating a silicone elastomer mixture by mixing equal amounts of the first and second silicone elastomers; and (4) applying the silicone elastomer mixture to a skin area.

Yet another method for treating skin, in accordance with one embodiment of the present invention, comprises: (1) providing a first silicone elastomer including: 50-80% by wt.

of a polydimethylsiloxane, 10-25% by wt. of a noncrystalline silicone dioxide, no more than 10% by wt. of a methylhydride crosslinker, 0.49-0.98% by wt. of a fumed silica, 0.25-0.49% by wt. of a cyclopentasiloxane, 0.03-0.09% by wt. of a platinum catalyst, and 0.18-0.49% by wt. of a hydroxyl terminated polymethylphenylsiloxane; (2) providing a second silicone elastomer including: 50-80% by wt. of a polydimethylsiloxane, 10-25% by wt. of a noncrystalline silicone dioxide, no more than 10% by wt. of a methylhydride crosslinker, 0.49-0.98% by wt. of a fumed silica, 0.25-0.49% by wt. of a cyclopentasiloxane, and 0.18-0.49% by wt. of a hydroxyl terminated polymethylphenylsiloxane; (3) creating a silicone elastomer mixture by mixing equal amounts of the first and second silicone elastomers; (4) stretching a wrinkled skin area to substantially smoothen the wrinkled skin area to a stretched skin area; (5) applying the silicone elastomer mixture to the stretched skin area; (6) holding the stretched skin area firmly until the silicone elastomer mixture hardens; (7) releasing the stretched skin area; and removing the silicone elastomer mixture.

It is an objective of the present invention to provide a skin treatment for managing skin conditions ranging from scars, including keloids, to burns and wrinkles.

It is another objective of the present invention to provide a means for a delivery mechanism of various treatments, medications, vitamins, herbal supplements, and other useful substances to treat the skin.

It is yet another objective of the present invention to provide a single treatment for both effectively treating and camouflaging scarred skin.

It is yet another objective of the present invention to provide a composition that cures on the skin with minimal cure times and requiring less frequent use, in order to encourage higher user compliance rates.

It is yet another objective of the present invention to reduce the frequency with which scar treatment compositions must be applied, in order to encourage higher user compliance rates.

It is yet another objective of the present invention to provide an elastomer that cures on the skin to create a substrate or film that compresses scars or wrinkles and facilitates skin treatment.

These and other advantages and features of the present invention are described herein with specificity so as to make the present invention understandable to one of ordinary skill in the art.

BRIEF DESCRIPTION OF THE SEVERAL VIEWS OF THE DRAWINGS

Elements in the figure have not necessarily been drawn to scale in order to enhance their clarity and improve understanding of these various elements and embodiments of the scar treatment and camouflage product. Furthermore, elements that are known to be common and well understood to those in the industry are not depicted in order to provide a clear view of the various embodiments of the invention.

DETAILED DESCRIPTION OF THE INVENTION

Figure 1A:
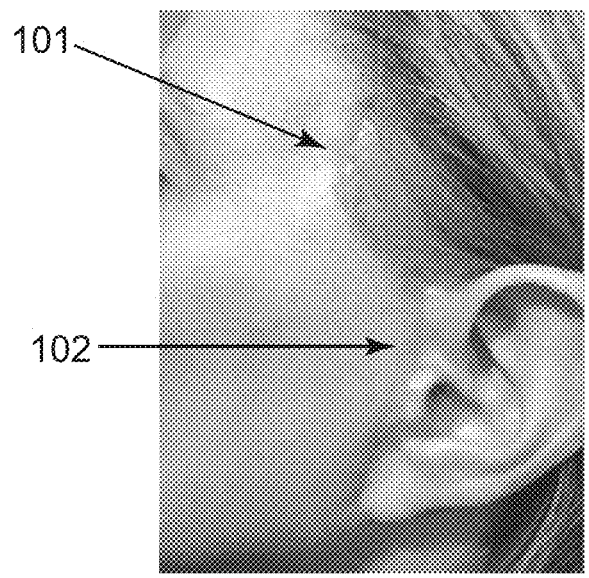
FIG. 1(a)-(b) depicts before (a) and after (b) photographs of a patient treated with a composition in accordance with the present invention.

The present invention addresses the need for a synergistic skin treatment. This treatment takes into account both the healing and cosmetic aspects of skin management, minimizing curing times and frequency of use, in order to encourage higher user compliance.

A skin treatment in accordance with the present invention may include a composition with one or more of the following components or layers: a cleansing solution component, a silicone elastomer component, and a mineral powder component. In exemplary embodiments, three layers or components may be used to treat and camouflage a scar: a solution for cleansing the skin, a silicone elastomer for treating the cleansed skin, and a mineral powder for further protecting and camouflaging the treated skin area. The cleansing solution component may be used to prime a damaged region of skin, cleansing and treating the region or skin area (i.e. with anti-inflammatories, anti-bacterial agents and other therapeutic properties) so that the silicone component can efficaciously heal the damaged skin. With aid from a catalyst, the silicone component may rapidly cure directly on the affected area of the skin. Because skin healing can take time, for example with more serious wounds, burns or scars, the mineral powder may be useful for further protecting and camouflaging the skin area as it heals. The mineral powder may include a setting powder to further hasten the curing of the silicone treatment on the skin area and give the cosmetic layer of the composition a soft texture—that feels like skin and removes the glossy appearance of the silicone. Furthermore, different ingredients may be delivered to the skin area with each layer or component. For example: the cleansing solution may include therapeutic ingredients such as anti-inflammatories and other substances to help prevent scars; the silicone component may be used as a delivery mechanism to provide the skin with botanicals, herbal medicines, over the counter medications, and other therapeutic substances; and the mineral powder may provide further protection such as UV protection as well as compatibility with other products including cosmetics.

In other exemplary embodiments, the silicone component may be used to smooth out wrinkled skin. The silicone component may itself comprise of a first silicone elastomer, and a complimentary or second silicone elastomer that has been treated with a catalyst in a manner so as to create an elastomer gel that cures directly on the skin. This silicone mixture forms a substrate or film that compresses the skin area. This embodiment of the invention allows a delivery mechanism for anti-aging topical products including other anti-aging solutions known in the art, in order to smooth the affected skin area and reduce or eradicate wrinkles.

Due to the nature of the compositions, treatment of damaged skin may be accomplished with the following advantages: less frequent product application, better resistance to smearing or rubbing off, implementation of an appealing fragrance or odorless compositions, strong water and ultraviolet resistance, painless application, effective delivery of various therapeutic substances, and cost effectiveness.

A particularly advantageous characteristic of the present skin treatment is that the silicone component cures quickly and directly on the skin. In the present disclosure, cure or curing may refer to the toughening or hardening of a polymer material by cross-linking of polymer chains, typically by application of heat or chemical additives such as a catalyst. Curing directly on the skin, therefore, eliminates the problems presented by prior art treatments such as sheeting or pads. These sheets or pads contain compositions already cured on a substrate, which the user must then apply to the skin. Complicating use of such prior art products, these pads or sheeting are not water resistant and must be removed and reapplied on a daily basis. The present treatment on the other hand, eliminates the need for sheeting since the silicone component cures directly on the skin to form a protective layer that can last up to a week. Because the user need not reapply the treatment on a daily basis, compliance rates are increased. To users of the present invention, this means that a brand-new treatment is provided each week, rather than applying a reusable silicone pad that has been washed, or may not have been washed prior to reapplication. The present invention avoids re-application of previously used medicated pads in order to prevent skin debris as well as bacteria or fungi from making contact with the treated area. Instead, the present skin treatment creates a brand-new silicone film or layer each time it is applied, fresh and without contamination.

To accomplish these and other advantages, various ingredients may be utilized, in addition to other additives from categories comprising: vitamins such as Vitamin A or Vitamin C and their corresponding derivatives; alpha hydroxy acids (AHAs); peptides; steroids; plant and herbal extracts; any medications such as, but not limited to, ayurvadic and Chinese herbal medications; hormones; analgesics; herbal supplements, and other useful substances (including over the counter medications) to treat the skin. These ingredients or additives may together exhibit at least the following properties: solvent, carrier, antiseptic, antimicrobial, anti-inflammatory, analgesic, antioxidant, or catalyst. These properties contribute to treatment of the skin insofar as treating damaged skin, whether the damage is due to burns, wounds, scarred skin, or undesirable wrinkles.

For example, anti-inflammatories and antioxidants diminish scar thickness and scar color by decreasing the biochemical cascade that promotes scar formation. Antiseptics are chemicals useful to sterilize a region of skin, i.e. kill microbial cells and spores. Along similar lines, antimicrobials tend to exhibit properties that prevent or inhibit microbial growth. Anti-inflammatory chemicals are useful to minimize inflammation of cells and tissue and with it any pain, discomfort, or itchiness caused by such inflammation. Thus, anti-inflammatory chemicals are also often analgesics, i.e. pain reducers. Antioxidants are chemicals that minimize chemical damage caused by free radicals. Antioxidants react with free radicals or their intermediaries to minimize their damaging effects. Catalysts decrease the activation energy of reactions and thus increase reaction speed, such as curing speed for the silicone-based composition.

As mentioned above, exemplary embodiments of a skin treatment in accordance with the present invention may comprise of a three layer treatment including a cleansing solution layer, a silicone elastomer layer, and a mineral powder layer. These layers or components of the treatment are discussed below in that sequence. After discussing each of these three distinct components, exemplary methods of preparing a treatment composition are disclosed, followed by disclosure of exemplary methods of applying a treatment composition to treat damaged skin.

Turning to the first component, a cleansing solution may be used to sterilize and cleanse a region of damaged skin that is to be treated. The surface of skin naturally contains debris, dead skin cells, various surface oils, salt, and various microorganisms (such as bacteria and fungi). Use of the cleansing solution permits the silicone component to better adhere to the region of the skin to be treated. Additionally, the cleansing solution minimizes trapping of unwanted bacterial and fungal spores and cells between the skin and the to-be-applied silicone component. Furthermore, the cleansing solution component may be used to treat a skin area by implementing anti-inflammatories, anti-bacterial agents and other substances with therapeutic properties. The cleansing solution may be applied to a region of skin before the silicone component is applied. The cleansing solution may be applied to a region of damaged skin by a brush, fingers, spray, or other techniques well-known in the art.

In an exemplary embodiment, the cleansing solution may comprise all or a combination of: isopropyl alcohol, colloidal silver, a catalyst such as a silicone platinum catalyst, chamomile extract, a curcumin derivative such as tetrahydrocurcuminoid, green tea extract, gotu kola extract, and *Boswellia serrata* extract. The botanical extracts may be organic or non-organic. Each of the enumerated components will be discussed in turn.

Isopropyl alcohol, also known as isopropanol and 2-propanol, may act as a solvent, carrier, and antiseptic. Isopropyl alcohol also acts as a solvent for surface oils on the user's skin, allowing the skin area to be cleansed of such surface oils and improve the efficacy of the silicone component.

Colloidal silver may serve as a solvent, carrier, and antimicrobial agent. Colloidal silver, like isopropyl alcohol, may help clean surface oils from the user's skin and improve the efficacy of the silicone composition.

A catalyst may be utilized to accelerate the cure time of an applied silicone elastomer. In an exemplary embodiment, the catalyst may be a silicone platinum catalyst. Such a catalyst may be an optional ingredient in the cleansing solution, may be used independently of any cleansing solution, included as an ingredient of the silicone component or mineral mixture, or may be omitted altogether from the cleansing solution component.

Chamomile is a flower of the Asteraceae/Compositae family and in medicinal applications two varieties are often utilized: German Chamomile (*Chamomilla recutita*) and Roman Chamomile (*Chamaemelum nobile*). Chamomile's medical properties are derived from the flowers yielding various terpenoids and flavonoids. In addition to chamomile extract's anti-inflammatory property, chamomile extract has astringent, penetration enhancing, skin soothing, and depigmenting properties. In some exemplary embodiments, organic chamomile extract may be preferred over non-organic sources of chamomile extract.

Curcumin, a polyphenol, and its derivative curcuminoids, are derived from plants of the turmeric family, a familiar spice. In addition to curcumin's anti-inflammatory property, curcumin can chemically "tan" skin, i.e. pigment or stain the skin. Thus, when curcumin is used with chamomile, curcumin's tanning property can offset chamomile's depigmentation property. In some exemplary embodiments, organic curcumin may be preferred over non-organic sources of curcumin. Additionally, in other exemplary embodiments the curcumin derivative used may be a tetrahydrocurcuminoid. Further, in an exemplary embodiment, the tetrahydrocurcuminoid may be of a cosmetic grade in a white powdered form, with the natural yellow pigment of curcumin removed or neutralized.

Green tea extract is derived from the leaves and stems of green tea (*Camellia sinensis*). Green tea extracts contain polyphenols which exhibit antioxidant properties. In some exemplary embodiments, organic green tea extract is preferred over non-organic sources of green tea extract.

Gotu kola (*Centella asiatica* and *Hdrocotyle asiatica*) is a semi-aquatic plant of the parsley family. Gotu kola is also commonly known as *centella*, pennywort, and Madekassol. The active medicinal chemicals in gotu kola are saponins and triterpenoids. Gotu kola extract exhibits antioxidant properties. In addition, gotu kola extracts may exhibit analgesic, sedative, antidepressant, antimicrobial, antiviral, and immunomodulatory properties. In some exemplary embodiments, organic gotu kola extract may be preferred over non-organic sources of gotu kola extract.

An alternative or additional source of anti-inflammatory and analgesic properties may come in the form of *Boswellia serrata* extract, an extract derived from the *Boswellia serrata* tree, also known as Indian frankincense, salai, and shallaki. In some exemplary embodiments, organic *Boswellia serrata* extract may be preferred. *Boswellia serrata* extract may be used in one of or both the cleansing solution and the silicone components, though in an exemplary embodiment, *Boswellia serrata* extract is a component of the presently discussed cleansing solution and absent from the silicone component.

TABLE 1

| Ingredient | Percentage Range by Weight |
| --- | --- |
| Isopropyl alcohol | .5-3% |
| Colloidal silver | 73-90% |
| Chamomile extract | 1-5% |
| Gotu kola extract | 1-5% |
| Green tea extract | 1-5% |
| Tetrahydrocurcuminoid | 1-4% |
| *Boswellia serrata* extract | 1-5% |

In an exemplary embodiment, shown on Table 1, the cleansing solution composition may comprise the following components by weight percentage: isopropyl alcohol (0.5-3%), colloidal silver (73-90%), chamomile extract (1-5%), gotu kola extract (1-5%), green tea extract (1-5%), curcumin extract (1-4%), and *Boswellia serrata* extract (1-5%).

In another exemplary embodiment, shown on Table 2, the cleansing solution may comprise the following components by weight percentage: isopropyl alcohol (5-15%), colloidal silver (70-90%), chamomile extract (0.5-5%), curcumin extract (0.5-5%), gotu kola extract (0.5-5%), green tea extract (0.5-5%), tetrahydrocurcuminoid (0.025-0.05%), and *Boswellia serrata* extract (0.5-2%).

TABLE 2

| Ingredient | Percentage Range by Weight |
| --- | --- |
| Isopropyl alcohol | 5-15% |
| Colloidal silver | 70-90% |
| Chamomile extract | .5-5% |
| Gotu kola extract | .5-5% |
| Green tea extract | .5-5% |
| Tetrahydrocurcuminoid | .025-.05% |
| *Boswellia serrata* extract | .5-2% |

Moving on to the next component, the silicone layer promotes cellular healing. The silicone component is designed to cure directly on the skin within a very short amount of time. The component or layer may be an elastomer that cures on the skin to create a substrate or film that compresses the skin area, for example a scar, burn, wound, or wrinkled skin requiring treatment. The silicone component works by compressing damaged skin and decreasing formation of blood vessels, fibroblasts, and scar tissue. For example, the silicone component may be applied to a scarred region of skin while the silicone is in an uncured liquid state, such as a gel. Once cured, the result is a layer or silicone-based film, which has been spread on and over the damaged skin region. This film provides a desirable thickness, and creates a type of second skin for the user, which means the layer does not cold flow or transfer to clothing or rub off. Furthermore, the silicone elastomer is no longer a flowing liquid, but a stable film that compresses on the skin tissue in order to continue to treat the damaged skin area. This gives the silicone component versatility as to its uses. For example, since it cures on the skin, the silicone component may stay on the user's skin for longer periods of time, which is required for treatment of scars (e.g. keloids) and more serious burns or wounds (e.g. gun-shot wounds). Alternatively, the silicone component or layer may be easily removed, in order to facilitate other treatments such as the treatment of wrinkled skin, which users may want to apply and remove daily.

In general, it is ideal to minimize cure times; hence, in various embodiments, the uncured silicone-based liquid properties, such as viscosity, may be varied to affect certain goals such as changing cure times. When cured to a tacky substrate (i.e. at approximately 60 seconds), application of the silicone component provides an ideal film to accept mineral powder for camouflaging the scar, including sunscreen ingredients for protecting the scar from UV damage.

The silicone component may be applied after or whilst the skin region is sterilized and cleansed by the above-described cleansing solution. Alternatively, preliminary application of the cleansing solution may be optional with respect to applying the silicone component. The silicone component may be applied to a damaged region of skin by brush, fingers, spray, or other techniques well-known in the art. Further, the silicone component need only be applied once every few days (about a week) to the region of damaged skin, which greatly increases user compliance over alternative topical gels and ointments which require the user to apply the treatment several times a day.

The silicone component may comprise a single solution or elastomer, or may comprise a plurality of elastomers that may be mixed together to achieve a mixture that cures on the skin with a fast cure rate. Whether a single mixture or multiple mixtures are used, the silicone component may include all or combinations of: a silicone elastomer, silica, dimethyl methylhydrogen siloxane copolymer, polydimethyl siloxane, hydroxyl terminated polymethylphenylsiloxane, *Boswellia serrata*, a catalyst, a cross-linker, and cyclopentasiloxane. Each of the above exemplary components of the silicone component will be discussed in turn.

The silicone elastomer may be a low consistency, low viscosity elastomer useful for curing as a thin, protective coating that may be incorporated over damaged skin. A suitable silicone elastomer may have a fast curing time with respect to many other scar-treating elastomers. This curing time may be improved by implementing or mixing in a catalyst with the silicone elastomer. In an exemplary embodiment, the silicone elastomer is a commercially available silicone elastomer. The silicone elastomer may comprise (by weight percentage): polydimethyl siloxane (50-80%), silica (10-25%), methylhydride crosslinker (less than 10%), and a silicone platinum catalyst (0.03-0.09%), wherein the silica is exemplarily non-crystalline. It will be understood that some similar or identical ingredients may be included in both the silicone elastomer and, more broadly, the silicone component, without deviating from the scope of the present invention. For example, in an exemplary embodiment, silica exists as an ingredient of the silicone component both within and outside of the silicone elastomer component.

Silica is also known as silicon dioxide. In an exemplary embodiment, the silica ingredient may be amorphous fumed silica, which may be available in powdered form. Amorphous fumed silica is a commercially available product. In the silicone component, amorphous fumed silica may be used as a filler or a means to adjust viscosity of the silicone layer of the skin treatment.

Polydimethylsiloxane is also known as dimethicone, PDMS, and E900. Polydimethylsiloxane is a type of silicone oil, a polymerized siloxane, and is used to produce a silicone-based elastomer. The surface of cured polydimethylsiloxane is hydrophobic, resisting swelling and wetting from water, making polydimethylsiloxane stable and suitable in aqueous environments.

Dimethyl methylhydrogen siloxane copolymer is also known as dimethyl siloxane-methyl hydrogen siloxane copolymer. Dimethyl methylhydrogen siloxane copolymer is used as a cross-linker to produce a silicone elastomer which is softer in the silicone elastomer's cured state.

Hydroxyl terminated polymethylphenylsiloxane is useful as a cross-linker which may aid in producing a softer cured silicone elastomer.

*Boswellia serrata* may serve as an anti-inflammatory and analgesic and may come in the form of *Boswellia serrata* extract. Embodiments may exist wherein *Boswellia serrata* is not an ingredient of the silicone component but rather provided separately as an ingredient to a cleansing solution for use prior to the silicone component.

The catalyst acts to speed up the silicone curing process to enhance convenience and compliance rates for users, as well as increase the tensile strength of the entire composition. In an exemplary embodiment, this catalyst may be a silicone platinum catalyst. With aid from the catalyst, the composition more quickly attains an even stronger resistance to environmental and physical disruption, such as contact with water or soap or the rubbing of fingers against the composition. Other catalysts maybe implemented, including a tin catalyst or a peroxide catalyst, without deviating from the scope of the present invention.

Cyclopentasiloxane is a silicone which is useful on account of its ability to act as a lubricant, solvent and filling agent, as well as its ease of spreading, silky texture, and its ability to increase the efficacy of heavier silicones like polydimethylsiloxane.

A number of additional additives may be used in the silicone component including, but not limited to: zinc, titanium, green tea powder or extract, and mineral pigments. Other such additives may be added to the silicone component without deviating from the scope of the present invention. In an exemplary embodiment, wherein a two silicone elastomer mixture is used that cures directly on the skin, one of such elastomers may be utilized as a delivery mechanism for any number of anti-inflammatory, anti-bacterial, anti-viral, or other botanical or medicinal agents or supplements that provide therapeutic effects depending on the user's treatment requirements.

In such embodiment, exemplary ingredient quantities of which are shown by Table 3 and Table 4, the silicone component may comprise of a mixture created by combining equal volumes of two separate silicone solutions or silicone elastomers—one including a cross-linker and the other including a catalyst—which when mixed cure directly on the skin.

For example, a first silicone solution or silicone elastomer may include (by weight percentage): silicone elastomer (96.97%-98.56%), silicone platinum catalyst (0.03-0.09%), silica (0.49-0.98%), cyclopentasiloxane (0.25-0.49%), hydroxyl terminated polymethylphenylsiloxane (0.18-0.49%), and dimethicone (0.49-98%). It is noted that in some embodiments of the composition, the silicone elastomer may already include between 50-80% by wt. of dimethicone or polydimethylsiloxane; nevertheless, it has been found to be advantageous to add an additional amount of polydimethylsiloxane in order to improve curing of the silicone component of the skin treatment. Similarly, adding a small amount of platinum catalyst to one of the silicone elastomers provides for a mixture that cures on the skin with improved efficacy. That is, even if utilizing a commercially available elastomer that contains a platinum catalyst, adding an amount (between 0.03 to 0.09% by weight) has proven to unexpectedly improve cure times, and enables an effective curing process to occur directly on the skin. Table 3 shows an example of ingredients and potential amounts in percentage range by weight of such first silicone elastomer for mixing with a second silicone elastomer:

TABLE 3

| Ingredient | Percentage Range by Weight |
| --- | --- |
| Silicone elastomer | 96.97-98.56% |
| Silicone platinum catalyst | .03-.09% |
| Silica | .49-.98% |
| Cyclopentasiloxane | .25-.49% |
| Hydroxyl terminated polymethylphenylsiloxane | .18-.49% |
| Dimethicone | .49-.98% |

A second silicone solution or silicone elastomer may include (by weight percentage): silicone elastomer (96.97%-98.56%), silica (0.49-0.98%), cyclopentasiloxane (0.25-0.49%), hydroxyl terminated polymethylphenylsiloxane (0.18-0.49%), and dimethicone (0.49-98%). (Table 3 represents the first solution and Table 4 represents the second solution, in accordance with one exemplary embodiment).

TABLE 4

| Ingredient | Percentage Range by Weight |
| --- | --- |
| Silicone elastomer (including a cross-linkler) | 96.97-98.56% |

TABLE 4-continued

| Ingredient | Percentage Range by Weight |
| --- | --- |
| Silica | .49-.98% |
| Cyclopentasiloxane | .25-.49% |
| Hydroxyl terminated polymethylphenylsiloxane | .18-.49% |
| Dimethicone | .49-.98% |

More specific approximations of exemplary weight percentage values seen in Table 4 are represented by Table 5 and are as follows: silicone elastomer (98%), silica (0.74%), cyclopentasiloxane (0.49%), hydroxyl terminated polymethylphenylsiloxane (0.25%), and dimethicone (0.49%), with small variations in weight percentage values still falling within the scope of the described exemplary embodiment.

TABLE 5

| Ingredient | Percentage by Weight |
| --- | --- |
| Silicone elastomer | 98% |
| Silicone platinum catalyst | .74% |
| Cyclopentasiloxane | .49% |
| Hydroxyl terminated polymethylphenylsiloxane | .25% |
| Dimethicone | .49% |

In yet other exemplary embodiments, the silicone component may comprise the following ingredients: silica, dimethicone, silicone platinum catalyst, dimethyl methylhydrogen siloxane copolymer, hydroxyl terminated polymethylphenylsiloxane, and *Boswellia serrata*.

Turning now to the third component, the mineral powder layer may be used to camouflage a region of the affected skin and treat that skin region by facilitating the curing of the silicone treatment on the skin area and give the cosmetic layer of the composition a soft texture—that feels like skin and removes the glossy appearance of the silicone. In addition, the mineral powder composition may also aid treatment of the skin by preventing sun damage to the skin and by preventing scar pigmentation, including hyper-pigmentation, caused by UV radiation. Further, the mineral powder, including various sunscreen ingredients, may be integrated into the silicone elastomer layer by applying the mineral powder to the silicone component layer before the layer has completely cured. Such integration is desirable and may result in the mineral powder possessing sunscreen that does not rub off on clothing or diminish the mineral powder's many properties such as: camouflage effectiveness; capacity to protect against UV radiation; color; and ability to weather exposure to water, such as in the shower, ocean, or pool.

Further, in exemplary embodiments of the mineral powder component, the mineral powder may uniquely and unexpectedly increase cure speed and tensile strength when applied to the curing silicone elastomer layer before the layer has cured.

Note in some exemplary embodiments, once the silicone elastomer layer is cured, said layer may not be washed off by soap and water. Further, when a mineral powder composition with sunscreen ingredients is integrated into the silicone component layer, the resulting layer may also not be washed off by soap and water.

The mineral powder composition may comprise all or combinations of: titanium dioxide, mica, magnesium stearate, zinc stearate, zinc oxide, natural mineral kaolinite, silica, iron oxides, calcium borosilicate, modified corn starch, caprylic capric triglyceride, honeysuckle extract, and vitamin E.

Mineral powder titanium dioxide, a plentiful and naturally occurring mineral, may be used as a white pigment, an opacifier, a thickening agent, a lubricating agent, and as a sunscreen.

Mica, also a plentiful and naturally occurring mineral, has desirable reflective and refractive properties providing a shimmery appearance to pigments used in mineral powder.

Magnesium stearate, a magnesium salt, has many uses in mineral powder including: anti-caking agent, binding agent, dusting additive, lubricating agent, emulsifying agent, gelling agent, thickening agent, and as lightweight filler to help increase adhesion.

Zinc stearate, a zinc salt, may be used in lieu of or in addition to magnesium stearate, and may serve as a lubricating agent, emulsifying agent, lightweight filler, thickening agent, and according to limited research, an astringent and antiseptic.

Zinc oxide, a naturally occurring mineral, provides mineral powder with thickening, whitening, lubricating, and sunscreen properties.

Natural mineral kaolinite is a silicate mineral which, in high enough concentrations, may be called kaolin or kaolin clay. Kaolin clay, also commonly referred to as white cosmetic clay, china clay, and ceramic clay, is used in mineral powder as a filler and adsorbent. Kaolin clay may be incorporated into a mineral powder composition as a fine powder.

Amorphous silica and/or hydrated silica (non-crystalline silica) may be used in the mineral powder to assist with moisture and oil absorption, i.e. used as a desiccant. As noted above in some exemplary embodiments of the silicone components, the silica used may be amorphous fumed silica, which in addition to having desiccant uses, may also be used for light-diffusing properties and as a thickening agent in cosmetic applications.

Iron oxides may be used in the mineral powder to create various skin-matching shades. While iron oxide is a naturally occurring mineral, the iron oxide used in the mineral powder component is preferable produced in a laboratory or other controlled setting because naturally occurring iron oxides often contain various undesirable contaminants. In an exemplary embodiment, the mineral mixture may comprise all or a combination of: yellow iron oxide, red iron oxide, and black iron oxide.

Calcium borosilicate may be used in mineral powder compositions in at least two common forms: calcium sodium borosilicate and calcium aluminum borosilicate. Chemically speaking, in both examples, calcium borosilicate is a member of the silica complex families. Such borosilicates are a glass generally insoluble in water. In mineral powder, these borosilicates may be incorporated into the mineral powder composition as flakes or microspheres and used as a bulky agent to reduce the bulk density of the mineral powder. Additionally, borosilicates may be used in mineral powder for their glass-like sheen and reflective properties so as to increase color and shine.

Modified corn starch may be utilized as a thickening agent, viscosity stabilizer, or emulsifying agent, and may be yield as a smoother, more desirable texture for application to the scar.

Caprylic capric triglyceride (also caprylic/capric triglyceride, caprylic triglyceride, and capric triglyceride), a specially esterified coconut oil, may be used to produce a silky, yet non-oily texture upon application. Caprylic capric triglyceride, as an oil substitute, may be ideal to interact with emulsifiers, as many emulsifiers lose a degree of efficacy in the presence of appreciable oil. Additionally, caprylic capric triglyceride is an excellent anti-oxidant with a low viscosity.

Honeysuckle extract is an extract originating from leaves, flowers, and buds of the *Lonicera japonica* plant. It may serve as an antibacterial, anti-inflammatory, antiviral, and antioxidant, and comprises flavonoids, saponins, triterpenoids, and tannins.

Vitamin E (tocopherol, or its ester, tocopheryl acetate) may be used as an anti-inflammatory, antioxidant, skin aging preventative, moisturizer, protector against damage from UV radiation, and promoter of healthy collagen in the skin.

In exemplary embodiments, the mineral powder may comprise a camouflaging component and a setting powder. In one of the exemplary embodiments, the camouflaging component and the setting powder are a single composition, applied together. In another of the exemplary embodiments, the camouflaging component and the setting powder may be separated, allowing a user to apply one or both of the components separately. This may be desirable, for instance, in such cases wherein a user wishes to capitalize on the quickened curing time afforded by the setting powder, but also wishes to incorporate the camouflaging component at a different time or use a different, personal camouflaging product.

The setting powder may be used to uniquely and unexpectedly accelerate the cure time and increase the tensile strength of an applied, but not fully cured, silicone component layer. To use these properties of the setting powder, the setting powder may be applied over the applied silicone component before the silicone layer has finished curing. The setting powder exemplarily comprises the enumerated natural mineral kaolinite and silica, as well as calcium borosilicate, although other embodiments exist wherein other setting powder ingredients may be used. In an exemplary embodiment, the silica used in the setting powder may be amorphous fumed silica, which facilitates the curing of the silicone treatment on the skin area and gives the cosmetic layer of the composition a soft texture that feels like skin and removes the glossy appearance of the silicone.

For example, the ingredients of an exemplary embodiment are shown on Table 6; the mineral powder component may comprise the following ingredients (by weight percentage): mica (55-68%), modified corn starch (12-25%), zinc stearate (3-8%), natural mineral kaolinite (3-6%), caprylic capric triglyceride (2-5%), zinc oxide (1-3%), honeysuckle extract (0.5-1.5%), vitamin E (0.5-1.5%), yellow iron oxide (0.5-1.5%), red iron oxide (0.1-0.3%), and black iron oxide (0.05-0.25%).

TABLE 6

| Ingredient | Percentage Range by Weight |
| --- | --- |
| Mica | 55-68% |
| Modified Corn Starch | 12-25% |
| Zinc stearate | 3-8% |
| Natural mineral kaolinite | 3-6% |
| Caprylic capric triglyceride | 2-5% |
| Zinc oxide | 1-3% |
| Honeysuckle extract | .5-1.5% |
| Vitamin E | .5-1.5% |
| Yellow iron oxide | .5-1.5% |
| Red iron oxide | .1-.3% |
| Black iron oxide | .05-.25% |

More specific approximations of exemplary weight percentage values seen in Table 6 are represented by Table 7 and are as follows: mica (62.2%), modified corn starch (18.5%), zinc stearate (6.5%), natural mineral kaolinite (4.5%), caprylic capric triglyceride (3.5%), zinc oxide (2%), honeysuckle extract (0.9%), vitamin E (0.8%), yellow iron oxide (0.8%), red iron oxide (0.2%), and black iron oxide (0.1%). It will be understood that variations to one or a few of the exemplary concentrations do not undermine the approximate concentrations of the remaining components of the mineral composition.

TABLE 7

| Ingredient | Percentage by Weight |
| --- | --- |
| Mica | 62.2% |
| Modified Corn Starch | 18.5% |
| Zinc stearate | 6.5% |
| Natural mineral kaolinite | 4.5% |
| Caprylic capric triglyceride | 3.5% |
| Zinc oxide | 2% |
| Honeysuckle extract | .9% |
| Vitamin E | .8% |
| Yellow iron oxide | .8% |
| Red iron oxide | .2% |
| Black iron oxide | .1% |

In other exemplary embodiments, the mineral powder may comprise the following ingredients: titanium dioxide, mica, magnesium stearate, kaolin clay, zinc oxide, silica, and iron oxide, and any other ingredient suitable for applying a cosmetic layer on an area of the skin in order to camouflage a scarred region.

Additionally, several other additives may be incorporated into one or more of the skin treatment components mentioned above using means well known in the art. That is, one or more of the components—the cleansing solution, the silicone elastomers and/or the mineral powder—may serve as a delivery mechanism for various treatments, medications, vitamins, herbal supplements, and other useful substances (including over the counter medications) to treat the skin. For example, and without deviating from the scope of the present invention, one or more of the following additives, supplements, medications, or ingredients, may be incorporated into one or more of the components above in therapeutically effective amounts. Note however, that when the additive or ingredient below is preferably implemented into the silicone component or layer of the skin treatment, it is preferably implemented with the silicone elastomer that excludes the platinum catalyst so that the additive or ingredient may better infuse with the silicone component. The following is a non-exhaustive list of such additives or ingredients that may be implemented:

*Acacia cathechu* (Katha) may be used as a natural coloring agent.

Alfalfa extract, or *medicago sativa*, may be used as a natural cleanser, mild exfoliant, and good source of minerals as well as vitamins A, B, C, D and E. *Medicago sativa* is rich in protein and contains saponins (natural foaming agents) that may be used to treat the skin as they are commonly used for face masks, bath oils, creams and lotions.

Algae extract or red algae blends—for example *Chondrus crispus* (Irish moss), Euchema and Gigartina, are high in iodine and amino acids. Algae extract is very nourishing and soothing to the skin and may be used as a thickener and stabilizer in cosmetic preparations.

*Symphytum officinale allantoin* extract from comfrey may be used in cell therapy treatments, including as a healing agent and moisturizer. It is commonly known as an anti-inflammatory and anti-irritant; the extract is reported to promote skin cell regeneration, and may be made from uric acid, but the comfrey root type is generally preferred. The finest quality is free of pyrrolizidine alkaloids.

Allspice refers to berries of an evergreen tree indigenous to the West Indies that is often ground and dried. It may be used as a skin tonic.

Almond butter, which is made from sweet almond oil, is a rich emollient and may be used as a skin conditioner.

Almond meal extract is a ground extract of the sweet almond kernel, which may be used in skin treatments as a mild exfoliant.

Aloe Vera oil is known as a healing agent for wounds and abrasions. It is considered one of nature's most effective remedies for sunburn and skin irritations, and a superb hydrator for skin. Aloe Vera juice has similar healing and soothing properties, in addition to having antibacterial and moisturizing properties. It may be used to relieve burning, itching, minor cuts and first and second degree burns. It is now known that aloe Vera has the ability to accelerate cell growth in the skin. Similarly, Aloe Vera fillets, or the gel-like substance that is removed from the aloe leaf, may be used as skin a soother and hydrator.

Alpha Olefine is a non-toxic, natural surfactant (cleansing agent) synthesized from vegetable extracts and castor oil, which may be used to cleanse an affected skin area.

Amber Essence is a proprietary blend of organic essential oils as well as a source of the highly sought after amber resin scent, which is a blend of *styrax* tree resin and essential oils extracted from the wood as well as the resin of various trees and plants.

In very large numbers, Amino Acids form proteins. Amino acids influence the health of the skin and some may help regulate oil production in the skin. Hence, delivering amino acids through a skin treatment may be useful in maintaining skin health. Amino Acid Complex (Cysteine, Methionine) is a set of sulfur-rich amino acids essential to protein metabolism, which is very nourishing to the skin. Together, these amino acids promote the regeneration of new skin cells and help regulate oil production in the skin.

Aminobenzoic Acid (PABA) is a water-soluble B vitamin that acts as a skin nutrient and sun protector, screening out the sun's damaging UV rays. Some people are sensitive to aminobenzoic acid, so a PABA ester (Padimate O) can be used as an alternative.

Both the oil and leaves of *Angelica archangelica* are very aromatic and may serve as skin soothing agents.

Annatto (*Bixa Orellana*) is a waxy extract from a South American shrub, used as a source of natural color. Naturally, it has a reddish-brown color, but becomes a deep red when mixed with an acid.

Apple Oil (*Pyrus malus*) is an apple peal extract combined with the juice from the pulp. The oil contains malic acid, which has antioxidant and pH adjusting properties, in addition to a pleasant fragrance.

Apricot Oil (from *Prunus armeniaca* tree), also referred to as persic oil, is an essential oil from apricot pits that serves as an emollient. It possesses a softening effect on the skin.

Apricot Kernels or Apricot Seeds (from *Prunus armeniaca* tree) may be ground into a powdered form and subsequently added to exfoliating masks and scrubs to achieve a smoothing effect on the skin.

Ascorbic Acid (Vitamin C) is an antioxidant and free-radical scavenger. Vitamin C is indispensable for the formation of healthy collagen, which reduces the appearance of wrinkles and keeps the skin looking young. It has also been shown to inhibit skin cancer.

Arnica Oil (*Arnica montana*) has nourishing and anti-inflammatory properties and, when combined with vitamin E, serves as a deodorant.

Atlas Cedar (*Cedrus atlantica*) is an aromatic essential oil with antiseptic and skin calming properties.

Avocado Oil (*Persea gratissima* or *Persea Americana*) moisturizes, nourishes, and softens skin. Unrefined Avocado oil, which is dark green in color, contains vitamins A, B1, B2, D, E, and Pantothenic acid, as well as lecithin. As a good source of vitamins A, D and E, amino acids and sterols, it is excellent for dry and wrinkled skin.

Aubrey's Preservative is a blend composed of citrus seed extract (from grapefruit seeds) which serves as a strong antioxidant as a result of an abundance of vitamin A, C and E. The preservative extends the shelf life of many products.

Balm Mint (*Melissa officinalis*) is an anti-irritant and mild sedative, making it ideal for sensitive skin Balm mint soothes and calms the skin, in addition to promoting healing.

Balsam Peru (*Myroxylon pereirae*) is an amber-colored essential oil with a rich, sweet vanilla-like aroma.

Balsam Tolu (*Myroxylon toluiferum*) is an antiseptic and antibacterial with healing properties often used in topical treatments and occasionally as a fragrance.

Basil (*Ocymum basilum*) is beneficial for its cleansing and relaxing properties, as well as its high concentration of Vitamins A and C.

Bay Lauryl Oil (*Laurus nobilis*) is an essential oil often used as a fragrance or skin or scalp tonic.

Bay Rum (*Pimenta racemosa*), also known as bay leaf is an essential oil which has a fresh scent and may be used a tonic for the skin.

Beeswax (*Apis mellifera*) is extracted from the honeycomb of honeybees and serves as a natural thickener and emulsifier.

Beet Root Extract (*Beta vulgaris*) is an extract of beets and may be used as a source of red pigmentation.

Benzoin Gum (*Styrax benzoin*), also referred to as Benzoin Bark, is a natural antiseptic, astringent, antioxidant and preservative that promotes healthy skin.

Bergamot Essential Oil is an essential oil of bergamot extracted from citrus fruit peels, which has antiseptic properties.

Beta-carotene may be used to create vitamin A, a vitamin known for promoting skin health.

Bicarb Soda (Sodium bicarbonate) may be useful for its mild abrasive, cleansing and whitening properties.

Biodynamic Avocado Oil (Unrefined Avocado oil) is a dark green oil containing vitamins A, B1, B2, E, and Pantothenic acid, as well as lecithin. It is excellent for dry and wrinkled skin.

Bilberry Fruit (*Vaccinium myrtillus*) is an astringent, tonic, and exfoliant.

Biodynamic *Macadamia* oil is a highly nourishing oil that helps reduce moisture loss from the skin and helps resist oxidation.

Biodynamic Tea Tree oil is a pure essential oil from Tea Tree leaves that serves as a potent antiseptic and antibacterial.

Biotin, also known as vitamin H, is an important factor in the proper functioning of the oil glands and in maintenance of moisturized skin.

Birch contributes to skin feeling soft and silky. Birch has antiseptic and aromatic properties beneficial to the skin.

Bitter Almond Oil (*Amigdalus communis*) is an essential oil used as a skin softener and a pleasant scent.

Bitter Orange Extract is a non-toxic natural antimicrobial with broad-spectrum activity.

Black Currant Extract (*Ribes nigrum*) is a source of natural fruit acids which is often used in face masks or lotions so as to encourage faster skin cell turnover.

Black Pepper (*Piper nigrum*) is an essential oil steam distilled from black peppercorns which may be useful as a tonic and antimicrobial.

Bladderwrack Extract (*Fucus vesiculosus*) is a seaweed, rich in alginic acid, amino acids, polysaccharides, minerals and vitamins that may act as both a stimulant and tonic.

Blueberry Leaves (*Vaccinium angustifolium*) may be used to make a mild, non-drying skin tonic.

Bluebottle (*Centaurea cyanus*), also known as Cornflower, is a moisturizing agent for the skin.

Blue Chamomile (*Matricaria chamomilla*), also known as German Chamomile, is a deep blue pigmented essential oil with a pleasant fragrance, which may serve as an antimicrobial and soothing tonic.

Blue Cypress Oil (*Callitris intratropica*) is an essential oil which serves as a natural disinfectant and freshener.

Blue Green Algae (*Aphanizomenon flos aquae*) is a good source of utilizable protein, enzymes, minerals, trace minerals and antioxidants. It is readily absorbed by the skin.

Borage Oil (*Borago officinalis*) is nutrient-dense oil that serves as an anti-inflammatory and soothing agent, especially beneficial for dry skin.

Burdock (*Arctium lappa*) is an antiseptic and antibacterial skin calming agent that may promote healing. Its root has been used as a remedy against skin cancer and is believed to reinforce smoothness of the skin.

Cade Wood Oil (*Juniperus oxycedrus*) is an essential oil used as a cleanser and toner.

Calaguala Fern Extract (*Polypodium leucotomos*) smoothes and conditions the skin and is useful as an additive to preparations for dry skin.

Calamine is a mix of zinc oxide and ferric oxide used in skin lotions and ointments for treating irritated skin.

Calcium Pyrophosphate is a mild abrasive useful for cleaning.

Calendula (*Calendula officinalis*), also known as Marigold, is useful for its healing, anti-inflammatory, and analgesic properties, as well as the presence of saponins. It is a common ingredient in ointments and natural deodorants and comprises a yellow pigmentation sometimes desired for beauty products.

Candelilla Wax (*Euphorbia cerifera*) is a wax derived from the Candelilla plant which possesses lubricating properties often useful in topical products.

Chamomile (*Anthemis nobilis*), also known as Roman chamomile, is a softening, hydrating, and calming agent for rough or dry skin.

Camphor Oil (*Cinnamomum camphora*) is a tonic used in lotions or creams for its cooling and soothing effects. It has anti-inflammatory and antiseptic properties.

Canadian Willowherb (*Epilobium angustifolium*) is an anti-inflammatory and soothing agent shown to be very effective in reducing skin itching and irritation.

Carrageenan Food (*Chondrus crispus*) is a seaweed gum serving as a natural stabilizer and emulsifier.

Carrot Oil (*Daucus carota* var. *sativa*) comprises seeds which yield an essential oil that is rich in beta carotene, a precursor to vitamin A. Carrot oil also contains high concentrations of vitamin E, which benefits skin cell regeneration and production of sebum.

Carrot Seed Extract has regenerating and toning effects, excellent for mature and congested skin.

Carrageenan Gum is a natural gum used for thickening, suspending and binding ingredients.

Castile Soap is a mild vegetable oil-based soap saponified with an alkaline salt good for cleaning skin surfaces.

Catnip Essential Oil is a perennial herb belonging to the mint family, the leaves of which have a stimulating effect.

Cayenne Pepper Extract (*Capsicum frutescens*) and its active ingredient, capsaicin, is a powerful analgesic, anti-inflammatory and warming agent, used to soothe tension, especially in the muscles.

Red Cedarwood Oil (*Juniperus virginiana*) is an essential oil known for its anti-irritant properties and its soothing effect on the skin.

Cellulose Gum is used as a binder and thickener in cosmetic products.

Celtic Sea Salt is a natural bath crystal rich in essential minerals.

Centaury (*Erythraea centaurium*), also known as Century Herb, is used in cosmetics for its soothing and astringent properties, as well as its ability as a topical to even out skin tones and discolorations. It may also be used as a natural color.

Chamomile Extract is used as an antimicrobial, and a calming and soothing agent for the skin.

Chamomile German Essential Oil (German Chamomile) has anti-bacterial and fungicidal properties and is very useful for as wound healer and analgesic.

Chamomile Roman Essential Oil (Roman Chamomile) is a pure essential useful as an antiseptic, astringent, healing agent, and anti-inflammatory for skin.

Chestnut Extract (*Castanea sativa*) may be used as a tonic and an astringent, as well as a natural brown pigment for cosmetics.

Chinese *Angelica* (*Angelica sinensis*), also known as Dong Quai, is an effective skin tonic and antibacterial used in preparations for skin conditions.

Chinese *Chrysanthemum* (*Chrysanthemum morifolium*), also known as Ju hua, is used to treat allergic reactions and skin irritations on account of its soothing effect on the skin.

Chinese Golden Thread (*Coptis chinensis*) is a natural antibiotic and immune system enhancer.

*Chlorella* (*Chlorella pyrenoidosa*) is a hydrating and soothing green micro-algae that contains all the essential amino acids, as well as high concentrations of chlorophyll, vitamin B, and natural mineral content.

*Chrysanthemum* (*Chrysanthemum roseum*), also known as Persian pellitory or painted daisy, is a natural astringent and skin revitalizer.

Cinnamon Leaf is an essential Oil with antimicrobial, astringent, soothing, and cooling properties.

Cinnamon (*Cinnamomum zeylanicum*) is a spice used as a coloring agent in natural makeup powders.

Citric Acid Extract from citrus fruits is used as a cosmetic pH adjuster.

Citric Seed Extract from citrus fruits is used as a preservative and a pH balancer.

Citronella is an essential oil good for oily skin and excessive perspiration.

Clary Sage Oil (*Salvia sclera*) is an essential oil with astringent and anti-wrinkle properties.

*Clematis* (*Clematis vitalba*) is an herb that, when applied topically, has anti-inflammatory and a soothing effect on the skin.

Clove Oil (*Eugenia caryophyllus*) is a soothing agent and antiseptic.

Clove Bud is an essential oil with antiseptic, stimulating and analgesic properties.

Cocoa Butter, derived from the cocoa bean, is a rich emollient for dry skin which softens and protects skin.

Coconut Fatty Acid Cream Base is an absorption base containing essential fatty acids, fatty alcohols, aloe vera and vitamins A, C and E. It is rich in linoleic and linolenic acids (vitamin F), which are excellent nutrients and skin conditioners.

Coconut Fatty Alcohols are derived from coconut palm kernels, which are natural emollients.

Coconut Milk (*Cocos nucifera*) is the milk that comes from coconuts, a natural skin hydrator.

Coconut Oil (*Cocos nucifera*) is a rich emollient which is converted into a soap through a saponification reaction.

Coconut Oil-Corn Oil Soap is a natural cleansing and foaming agent serving as a mild detergent, similar in composition to saponins from soap bark and *yucca* root.

Coco betaine is a foaming agent derived from coconut oil.

Coco polyglucose is a mild foaming agent particularly suited to cause very little skin irritation.

Collagen Dermal is a protein that makes up 70 percent of the body's connective tissue. Thus, when it is applied topically, it helps attract and retain moisture to smooth and soften the skin.

Coltsfoot (*Tussilago farfara*) is a skin nutrient that is high in polysaccharides, vitamin C, and zinc, which acts as an anti-inflammatory and soothing agent, and a skin regenerative.

Corn Cob Meal (*Zea mays*) is a powder obtained from ground dried corn cobs, added to masks and scrubs for its pore-clearing and exfoliating properties. Sometimes used as a thickener.

Corn Meal (*Zea mays*) is meal obtained from ground corn, which may be used as a thickener and exfoliant in cosmetic formulations, as well as a source of skin soothing and softening.

Corn Starch is a powdery flour useful as a chelating agent and an emulsifier.

Corn Syrup is a chelating agent also useful as an emulsifier and humectant.

Cucumber (*Cucumis sativa*) is used in many topical products as an astringent and a soothing and cooling agent. It is rich in vitamin C, and thus a good antioxidant, and is a good skin nutrient.

Cypress Blue Australian Essential Oil (and other similar names) is an antibacterial, astringent, anti-inflammatory, anti-irritant, anti-viral, and a fixative.

Cysteine is an amino acid rich in sulfur, which is beneficial to the skin.

D-Alpha Tocopherol (Vitamin E) protects the skin from damage and cancer, serving as a powerful free-radical scavenger. Additionally, Vitamin E extends cell life, thereby protecting against premature aging and wrinkles.

D-Panthenol (Vit B5) Panthenol is the provitamin of pantothenic acid (vitamin B5). It improves the skin's moisture-retention capacity, stimulates skin regeneration, and serves as an anti-inflammatory and anti-itching agent.

Decyl glycoside is a non-toxic foaming agent synthesized from glucose from sugar.

Deionized Water is purified water that has had ions removed, and which may also have removed other undesirable compounds or heavy metals.

Desert Herb Complex is an herbal blend of organic jojoba, aloe, and *yucca* root extract, which may together help keep skin moist and calm.

*Echinacea* (*Echinacea angustifolia, Echinacea purpurea*), also known as Coneflower, calms, revitalizes, stimulates, and purifies skin, as well as exhibits antibacterial, antifungal, anti-wrinkle, hydrating, and firming properties.

Eclipta alba (False Daisy) is used as a natural coloring agent.

Egg Oil is rich in natural emulsifiers and serves as an excellent emollient, moisturizer, skin soother, skin texture smoother, and humectant.

Elastin is one of the three primary proteins found in the skin (along with collagen and reticulin) and is thus an essential component of skin health.

Elder Flower and Elder Berries (*Sambucus nigra*) are excellent skin softeners high in fatty acids for promoting healthy skin.

*Emblica officinalis* (Indian Gooseberry) is used as a natural coloring agent.

Essential oils are volatile liquids extracted from plant materials which have a familiar and characteristic plant aroma. Essential oils do not leave an oily residue on the skin.

Ester-C® Topical is a form of natural vitamin C, clinically shown to retain potency longer than other forms of vitamin C. As a stable vitamin C source, it is able to serve as an excellent antioxidant which penetrates into deep layers of the skin to promote collagen production.

*Eucalyptus* Oil (*Eucalyptus globulus*) is an essential oil often used in many cosmetic treatments with strong antiseptic, antibacterial, antifungal, cooling, and soothing properties.

*Eucalyptus*-Blue Mallee Essential Oil serves as antiseptic, stimulant, and decongestant for skin.

Evening Primrose Oil (*Oenothera biennis*) is a strong emollient and skin nutrient, with a high concentration of essential fatty acids and gamma-linolenic acid (GLA), It is effective in treating dry skin or other similar conditions.

Evergreen Oil (*Magnolia grandiflora*) is a mild astringent and tonic that demonstrates a cooling effect on the skin.

Everlasting Oil (*Helichrysum italicum*) is an essential oil that often serves as a pleasant fragrance.

Eyebright (*Euphrasia officinalis*) is an astringent and tonic that exhibits anti-inflammatory properties.

Fatty Acid Esters are waxes derived from plants and animals that may be used in absorption bases and as emulsifiers. Jojoba oil (wax) and lanolin from wool are examples.

Fennel Essential Oil, made from crushed Fennel seeds, increases the elasticity of the connective tissues of the skin, and its tightening effect on the skin is useful as anti-wrinkle and anti-aging ingredients.

Feverfew (*Chrysanthemum parthenium*) is an analgesic and anti-inflammatory. This ingredient is useful for relieving pain and swelling of insect bites, rashes and other skin irritations when topically applied to the skin.

Flaxseed Lignans are phytonutrients found in flaxseeds and are known as having antioxidant, anti-inflammatory and oil-balancing properties when applied topically to the skin. Flaxseed Lignans may be used on skin treatment components to prevent acne and clogged pores and reduce ingrown hairs and skin bumps caused by shaving.

Flaxseed Oil is an emollient and anti-inflammatory, which is high in essential fatty acids, B vitamins, protein and minerals. Flaxseed oil may be applied topically to provide nourishment to dry skin.

Forsythia Fruit (Forsythia suspense) is an anti-inflammatory and astringent, and may be used topically as a soothing agent for the skin.

Frangipani Absolute (*Plumeria obtuse*) is a desirable scent and may be used as a fragrance.

Frankincense Essential Oil is regenerative and astringent, and tones the skin and promotes new cell generation. This ingredient may be used to treat aging skin and wrinkles.

French Cypress is the pure essential oil of the Cypress leaves and twigs and has a tightening effect on the skin in general.

French Lavender is useful for regulating sebum production and fosters the regeneration of new skin cells. It may be used to soothe inflamed skin.

Fructose, a sugar found in fruits and honey, may be used to soothe, hydrate, and encourage moisture retention in the skin.

Fruit Acids are a group of acids naturally occurring in fruits and herbs. Similarly, Alpha-hydroxy acids, a patented form of fruit acids, are well known for enabling exfoliation and rapid turnover of skin cells. Some natural sources for fruit acids include bilberry herb, black currant, grapefruit, tomato, wine and grapes (glycolic, malic, pyruvic, benzylic, citric, tartaric and lactic acids). Either natural or synthetic solutions may be implemented to be used to clear and smooth skin complexion.

Fumitory (*Fumaria officinalis*) is a tonic and purifier, and may be used to achieve a brightening effect on the skin.

Garnet, (water-polished alluvial garnet) is a natural exfoliant that may be implemented, for example, on the cleansing solution.

Geranium (Rose) Oil is an astringent useful for softening and soothing skin. The pure essential oil obtained from the Geranium leaf and stem is antiseptic, astringent and toning. It normalizes sebum production and stimulates the lymphatic system, thus useful for treating seborrhea, rosacea, inflamed skin and other dermatological conditions.

Geranium Oil (*Pelargonium graveolens*) is an essential oil with astringent and tonic properties, which may be used to normalize oily skin and serve as a fragrance.

Ginger (*Zingiber officinale*) is an anti-inflammatory and stimulant. Additionally, ginger has useful properties such as warming and soothing the skin when applied topically. Ginger promotes circulation to the skin and may be implemented in both powdered and essential oil form. Ginger may also be used as a fragrance.

Ginkgo Leaf Extract (*Ginkgo biloba*) is an anti-inflammatory and antiallergenic, useful for soothing the skin.

Ginseng Root (*Panax Ginseng*, Asian; or *Panax quinquefolium*, American or; *Eleutherococcus senticosus*, Siberian) is a stimulant and tonic containing saponins.

Glucose is a fruit sugar from corn and grapes which soothes and hydrates skin and encourages moisture retention.

Glycerol monosterate is derived from vegetable oils and may be used as an emollient, emulsifier, antimicrobial, and preservative.

Glycolic Acid is a fruit acid from sugar cane and other sources, often used in exfoliating masks and lotions to help remove dead skin cells and promote new cell growth.

Glycogen is a sugar-based carbohydrate (polysaccharide) the body uses for energy storage.

Glycoprotein is a protein linked to a polysaccharide (glycogen), which contains sugars and amino acids that help strengthen and smooth hair fibers.

Goa Herb (*Andira araroba*) is a natural astringent, useful for the treatment of acne, eczema and other skin conditions. Goa Herb is also a calming agent for itching, flaking or irritated skin.

Gotu Kola Extract contains anti-wrinkle, anti-aging, and healing properties. Gotu Kola is useful for stressed skin, as a skin tonic, and for healing wounds, dermatitis, and inflammations.

Grape Seed Extract (*Vitis vinifera* extract) is a powerful antioxidant high in proanthocyanidins. Grape seed extract helps prevent skin cell damage caused by sun exposure and pollution.

Grape Seed Oil is an antioxidant-rich oil cold-pressed from grape seeds, particularly useful for treating baby skin. It is commonly used for massage blends because of its light texture, and lack of color and odor. It is suitable for all skin types and has a high level of polyunsaturated fatty acids.

Grapefruit Extract has potent antibacterial and anti-fungal properties and can be used as an internal medication to relieve *Candida* infections.

Grapefruit Oil (*Citrus paradise*) is an essential oil extracted from the peel of a grapefruit, which may be used for its astringent and skin-freshening properties as well as its fragrance.

Green Clay (Montmorillonite Clay) is rich in minerals and other nutrients, and may be used to draw out impurities, as well as to balance and clear the skin.

Green Tea (*Camellia sinensis*) is an antioxidant that inhibits the formation of cancer-causing free radicals and helps prevent skin cell damage caused by sun exposure and pollution. It is also a soothing and moisturizing, anti-inflammatory, and anti-irritant agent, high in xanthenes.

Guar Gum is a natural gum derived from the Guar plant, used as a thickening agent. Similarly, Gum Arabic (*Acacia gum*) is another herbal gum used as a thickener and emulsifier.

Gum Tragacanth (*Astragalus gummifer*) is another thickener and binding agent; a natural alternative to synthetic polymers (such as PVP) found in most commercial hair products.

Hazelnut Oil contains vitamins, minerals and protein and may be used for the treatment of skin.

He Shou Wu (*Polygoni multiflori*) is a scalp stimulant and tonic used in traditional Chinese medicine to refresh and energize the scalp, minimize hair loss and prevent or reverse graying hair.

Hematite Iron oxide is a mineral useful as a coloring agent varying in color from reddish-brown to black.

Henna Extract (*Lawsonia inermis*) is another ingredient useful as a coloring agent varying in color from reddish-brown to black.

Honey Light is a humectant and nutrient used as a thickening agent.

Hops (*Humulus lupulus*) is an antimicrobial and sedative, very soothing and toning to the skin. Combined with chamomile, it reduces swelling and relieves itching and irritation of the skin.

Horsechestnut Extract is useful for decongesting and draining broken capillaries. Similarly, Horsechestnut seed provides a desirable treatment for blotchy, sensitive skin because it helps to strengthen capillaries. It is also an anti-inflammatory, anti-irritant and mild astringent that helps stimulate circulation to the skin. Furthermore, it has sedative properties.

Horsetail (*Equisetum heymale, Equisetum arvense*) is nutrient-rich and high in silica, essential to collagen production. Often used as a vegan alternative to collagen treatments, it firms and refreshes the skin and promotes healing.

Hydrolyzed Elastin is a water-soluble protein of bovine origin, which may be used topically to help attract and retain moisture to smooth and soften the skin.

Hydrolyzed Soy Protein is a water-soluble protein that may be used topically as a hydrator, which improves the texture and resiliency of the skin.

Hydrosols or floral waters are byproducts of the steam distillation of plant materials, which may be beneficial to skin.

Hydroxymethylglycinate is a non-toxic anti-microbial agent derived from glycine (a natural preservative), which in turn is extracted from plants.

*Indigofera* (*Indigofera tinctoria*) is a safe natural plant color (deep blue to purple), which may be utilized for its antiseptic properties.

Inositol is a B vitamin useful for cell respiration; it helps maintain skin health.

Iodides are compounds containing iodine, which may be used topically for their antiseptic properties.

Iron Ivy (*Hedera helix*) is an anti-fungal often found in massage lotions and anti-cellulite preparations for its skin-toning and firming properties. It contains malic acid, a natural fruit acid that encourages skin cell turnover.

Jasmine Oil (*Jasminum officinale*) may be used as an aromatic for its calming effect and natural fragrance. Furthermore, it is useful as a soothing agent for skin.

Jojoba Meal (*Simmondsia chinensis*) contains high levels of protein and natural fibers. It is a byproduct of the moisture-rich jojoba plant, which contains 17 amino acids. Its mild exfoliating properties help clear away dead skin cells and nourish and deep-cleanse the complexion without drying it out. Jojoba Butter is natural butter made from jojoba oil, useful as a skin emollient. Similarly, Jojoba beads may be used as a very mild exfoliant. Also related, Jojoba Oil, Jojoba Wax (*Simmondsia chinensis*) is a waxy oil extracted from the bean, which acts as a humectant, in addition to creating a protective film over the skin thereby helping seal in moisture. The oil is highly stable and very effective on dry skin.

Jojoba Wax Spheres are made from jojoba wax, and are perfectly smooth microscopic beads that act as gentle exfoliants in masks and scrubs. It is a natural alternative to polyethylene beads (plastic) found in some skin care products.

Juniper Berries (*Juniperus communis*) may be used as a toner and antiseptic to treat oily skin and acne, as well as eczema and other chronic skin conditions. Furthermore, Juniper Berries may be used as a fragrance.

Kakadu plum (*Terminalia fedinaniana*) is a Kakadu plum extract with an incredibly high concentration vitamin C, making it useful as a skin tonic.

Kaolin (Mt. Kaolin Clay) is a fine, natural clay used in deep-cleansing face masks.

Kava Kava (*Piper methysticum*) is a mild sedative and analgesic that soothes and relaxes overworked muscles, thus serving as an excellent ingredient for massage lotions and bath oils.

Kelp (*Macrocystis pyrifera*) is a seaweed high in iodine and vitamins A, B-complex, C and E, which is soothing and toning for the skin.

Korean *Ginseng* is a potent skin re-activator and rejuvenator, which activates cell metabolism and prolongs the life span of human cells. Thus, it is useful as anti-wrinkle and anti-aging ingredient, as well as an anti-inflammatory.

Kukui Nut Oil (*Aleurites moluccana*) is rich in essential fatty acids and serves as a natural moisturizer and skin protector.

Lactalbumin is a milk protein high in lactic acid and which contains the eight essential amino acids.

Lactic Acid is a rich moisturizer which produces pH levels typical of skin.

*Laminaria* (*Laminaria digitata*) is a type of seaweed high in antioxidants and iodine that helps attract and retain moisture on the skin (humectant).

Lanolin is the sheep wool oil that is used as an absorption base in moisturizers.

Lavender-Glycerin (*Lavandula angustifolia*) is a strong soothing for the skin.

Lavender Oil (*Lavandula angustifolia*) is an essential oil added to skin care preparations for its soothing and antiseptic properties and pleasant fragrance.

Lavender Water (*Lavandula angustifolia*) is a natural hydrating and soothing agent, as well as an anti-irritant and antiseptic, often used in facial cleansers, toners and lotions for sensitive skin.

Lecithin is a vegetable extract high in natural fatty acids.

Lemon Essential Oil is a pure essential oil acting as an astringent, antibacterial, antiseptic and cleansing agent which, if applied to oily skin, can help reduce sebum production.

Lemon Myrtle Essential Oil is an astringent, antibacterial, antibacterial, and antiseptic which is excellent for repairing skin, acne conditions, and oily skin.

Lemon oil is a pure essential oil acting as an astringent, antibacterial, antiseptic and cleansing agent which, if applied to oily skin, can help reduce sebum production.

Lemon Peel Oil (*Citrus limonum*) is an essential oil with antioxidant and antibacterial properties, often used in cosmetics as a skin freshener and pleasant fragrance.

Lemongrass (*Cymbopogon citratus*) is an antimicrobial, antioxidant, and antifungal often used as a fragrance. It is an excellent normalizer for oily skin.

Lime Oil (*Citrus aurantifolia*) is an essential oil from the peel of the lime which acts as a natural antiseptic and tonic, and may be used as a pleasing scent.

Linden Extract (*Tilia cordata*) contains an essential oil, farnesol, which is similar to aloe and chamomile, which acts as an emollient and soothing agent for the skin.

Liposomes are used in creams and lotions, as they penetrate skin easily to deliver nutrients, moisture and other substances to the skin.

Liquorice extract (*Liquiritia officinalis*) has skin soothing, rejuvenating, and nutritive properties.

Lysozyme is a natural enzyme for lowering activation energy required for many reactions pertinent to skin compositions.

*Macadamia* Nut Oil (*Macadamia ternifolia*) is an excellent moisturizer and skin protector, high in essential fatty acids. It has a natural affinity to human sebum which makes it an excellent skin care ingredient.

Magnesium is a mineral crucial for nutrition and absorption of calcium and vitamin C which, when applied topically, helps regulate oil production in the skin.

*Magnolia* Blossom Extract (*Magnolia acuminate*) is a natural tonic and anti-irritant with a mild bleaching effect on the skin, sometimes used as a fragrance.

Mallow (*Malva sylvestris*) is a natural hydrator with skin-softening properties that is often found in topical creams, lotions and facial masks for dry skin.

Mandarin Orange Peel Extract (*Citrus reticulate*), also known as Ju pi/chen pi, is a natural anti-inflammatory, and promoter of skin circulation, which helps to fade skin imperfections.

Mango Butter (*Mangifera indica*) is butter made from the seed of the mango, which serves as an excellent moisturizer.

Manuka Oil (*Leptospermum scoparium*) is an analgesic, antifungal and antibacterial with a pleasant, honey-like fragrance.

Marshmallow Root (*Althaea officinalis*) is an excellent hydrator and skin soother that helps soften, protect and regenerate skin.

Marshmallow Root Extract softens, revitalizes, and hydrates skin, as well as acting as an emollient, anti-inflammatory, and soothing and healing agent.

Meadowsweet (*Spiraea ulmaria*), also known as Lady of the Meadow and Meadow Queen, is used in cosmetics for sensitive skin on account of its mild, tonic effect.

Menthol Oil is an antiseptic and astringent with warming/cooling properties that have a soothing effect on the skin.

Methionine is a sulfur-rich amino acid that is very beneficial to the skin.

Mica is a transparent mineral used to provide slip, light reflection, and shimmer in cosmetics.

Milk Thistle (*Silybum marianum*) comprises flavonoids with strong antioxidant and soothing properties.

Mint may be a variety of aromatic plants (genus *Mentha*) which are used as natural antiseptics and fresheners and sometimes fragrances.

Mistletoe (*Viscum album*) is an anti-irritant, with soothing properties for sensitive skin. It is often combined with fennel, hops, chamomile, balm mint and yarrow in skin formulations.

Moroccan Rose oil is excellent for dry, mature and sensitive skin and serves as an astringent, and toning and regenerative agent.

*Morus* Root (*Morus alba*), also known as Sang-pai-pi, has anti-inflammatory and humectant properties and is soothing on the skin.

Mucopolysaccharides are used in skin formulations for their ability to retain water. Mucopolysaccharides from aloe vera are the preferred mucopolysaccharides.

Myrrh Essential Oil is a pure essential oil that has excellent anti-aging, regenerative, moisturizing, and anti-wrinkle properties, and serves as an astringent that promotes new cell generation. It is sometimes used as a fragrance.

Myrtle Herb Extract (*Myrtus communis*) is an aromatic stimulant and mild tonic used in suncare products for its soothing effect on irritated skin.

Native Thyme (Thymus Native Thyme) is known for its cleansing, anti-bacterial and purifying properties, and is generally refreshing to the skin.

Natural Cetyl alcohol is a natural thickener, emulsifier and carrying agent.

Natural Flower Oil is used in perfumes and colognes as a natural fragrance.

Natural Grain Alcohol is an antiseptic that serves as a less harsh, less drying compound than isopropyl alcohol.

Natural Gum is a natural polysaccharide obtained through fermentation of a glucose-enriched medium by *Sclerotium rolfsii*.

Neem Extract has anti-aging, anti-fungal, and soothing properties.

Neroli Essential Oil is known to regenerate skin cells and improves skin elasticity, as well as help prevent acne and scarring.

Nettle (*Urtica dioica*), also known as Stinging Nettle, is an excellent tonic and astringent, rich in phosphates and trace minerals, that promotes circulation to the skin.

Niacin (Vitamin B-3) is essential for blood circulation and healthy skin.

Nutmeg (*Myristica fragrans*) is an essential oil used in cosmetics for its exotic, spicy fragrance.

Oatmeal (*Avena sativa*) is a cleanser, toner, mild exfoliant and excellent addition to facial masks. It helps fade age spots and other skin imperfections and even out skin tones.

Oat Protein (*Avena sativa*) is a humectant shown to increase hydration and smooth fine lines and wrinkles.

Olive Extract is used to repair, tone, and firm skin, and serves as an anti-oxidant and hydrating agent, as well as a reducer of skin damage from UV radiation.

Olive Kernel Powder (*Olea europaea*) is a mild exfoliant derived from olive seeds.

Olive Leaf Extract (*Olea europaea*) is used for its anti-bacterial properties.

Olive Oil (*Olea europaea*) is a rich emollient high in oleic acid, used in skin care preparations for its softening and smoothing properties.

Olive Oil Castile (*Olea europaea*) is saponified with an alkaline salt and becomes an excellent soap which is mild and soothing to the skin.

Orange, Sweet Essential Oil is a pure essential oil from the peel of ripe oranges that serves as an astringent, anti-bacterial, antiseptic, toning and cleansing agent.

Orange Blossom Oil (*Citrus aurantium*), also known as Neroli, is an astringent aromatic oil obtained from orange blossoms, often used as a fragrance.

Orange Pith Juice (*Citrus sinensis*) is high in vitamin C and pectinic acid, and helps lock in nutrients.

Organic Rosehip Oil, Rosehip Seed oil is high in vitamin F and is used to reduce soften scarring and facial lines and slow skin aging.

Organic Safflower Oil is used as a carrier for essential oils which spreads easily on any skin type and has an incredibly high linoleic acid content and strong moisturizing capability.

Organic Sesame oil (*Sesamum Inicum*) is high in mineral content and consists essentially of oleic and linoleic acids, both of which are beneficial to the skin.

Organic Vanilla extract is used for its pleasing aroma.

Oregano Oil (*Origanum vulgare*) is a powerful antifungal, healing, soothing, and anti-irritation agent.

Padimate O is an ester of aminobenzoic acid shown to protect skin from the sun's harmful UV rays, thus serving as an effective sunscreen.

Palm Oil (*Elaesis guineensis*) is saponified with an alkaline salt and used in production of bar soaps.

Palma *Rosa* Oil (*Cymbopogon martini*) is an essential oil used for its pleasant scent and hydrating and tonic effects on the skin.

Palmitate is a salt or ester of palmitic acid, and is often used in baby oils, bath oils, and moisturizers.

Panthenol (Vitamin B-5) is an excellent skin hydrator, also sometimes known as Pantothenic Acid.

*Papaya* (*Carica papaya*) is an excellent skin softener and mild exfoliant.

Passionflower (*Passiflora incarnate*) is an analgesic, anti-irritant and sedative, and its roots and leaves are used in skin care formulations for their soothing properties.

Patchouli (*Pogostemon cablin*) is an aromatic essential oil often in many fragrances used to treat dry, mature or wrinkled skin, and to rejuvenate, invigorate and restore skin.

Peanut Oil (*Arachis hypogaea*) is a superb emollient often used in natural massage oils and soaps.

Pectin is used to help lock in nutrients and enhance shine.

Pellitory (*Anacyclus pyrethrum*) is a pungent herb used as a stimulant and circulation enhancer.

Pellitory-of-the-Wall (*Parietaria officinalis*) is an herbal extract with emollient and astringent effects sometimes combined with the mallows elder and *arnica* in moisturizers.

Pennyroyal (*Mentha pulegium*) is a strong purifier and antiseptic.

Peony Herb, Peony Root (*Paeonia lactiflora*) is an antibacterial, antifungal and anti-inflammatory used in acne and facial preparations.

Peppermint Oil (*Mentha piperita*) is an excellent antiseptic, anti-inflammatory, and soothing agent often used in bath oils for its warming and cooling properties on sore muscles.

Phospholipids are fatty substances that are used to make liposomes, which act as delivery agents for vitamins and humectants.

*Pimenta* Leaf Oil (*Pimenta officinalis*) is an essential oil with antiseptic and astringent properties, and may also serve as a tonic with a pleasing fragrance.

Pine Needle Extract (*Abies siberica*) or, more broadly, a pine-tree, is often blended with witch hazel, red vine and other herbals for to produce tonic, antiseptic and stimulating effects on the skin. Additionally, it is often combined with hops, rosemary and horsetail to serve as an addition to cell therapy moisturizers.

Pine Tar (*Pinus sylvestris*) soothes dry skin.

Plantain is an astringent with soothing and healing capabilities which reduces oil secretions of the skin.

Red Vine (*Vitis vinifera*) has soothing, anti-redness, anti-irritation, anti-inflammatory, antioxidizing, and toning properties, and has the ability to limit blotchiness of skin treatments. It is high in vitamin C, choline and inositol.

Reticulin is one of the three main proteins found in the skin, and is often used in cellular repair products (often topical) for its ability to attract and retain moisture (humectant).

Riboflavin (Vitamin B-2) is an antioxidant B vitamin crucial to production of glutathione, which protects skin cells from free radical damage.

Roman Chamomile Oil (*Anthemis nobilis*) is an anti-inflammatory and skin-soother.

*Rosa* Mosqueta® Rose Hip Seed Oil (*Rosa rubiginosa*) is an oil high in vitamin C, and linoleic and linolenic acids, good for its healing and moisturizing properties. Clinical tests have shown that it can help fade scarring and skin discolorations and encourage skin cell growth.

Rose Geranium (*Pelargonium roseum*) is an essential oil used in skin care for its soothing and aromatic properties.

Rose Oil (*Rosa damascene*), also known as Rose Otto, is an essential oil used for its skin softening properties and pleasant fragrance.

Rosehip Seed Oil regenerates, moisturizes, and heals skin, scars, and facial lines with help from the high concentration of vitamin F.

Rosemary Extract is an antioxidant, antibacterial, soothing and wound healing agent.

Rosemary Oil (*Rosmarinus officinalis*) is an essential oil with antioxidant, toning and purifying properties.

Rosewater (*Rosa damascene*) is a natural hydrator and anti-irritant used in cosmetics as a soothing agent for dry, sensitive skin.

Rosewood (*Aniba rosaeodora*), also known as Bois de Rose, is an essential oil with a pleasant fragrance which has mild analgesic and stimulating properties.

Royal Jelly is a powerful nutrient high in amino acids, minerals and vitamins A, B, C and E that is very soothing and moisturizing to the skin.

Safflower Oil (*Carthamus tinctorius*) is rich in skin-soothing oleic acid and vitamin E.

Sage Oil (*Salvia officinalis*) is a purifier, tonic, antioxidant, and antibacterial agent that is very beneficial to the skin and in skin treatment preparations.

Sage Extract is an antibacterial, soothing, deodorant and strengthening agent.

Sandalwood Oil (*Santalum album*) is a very old fragrance staple.

Saponin is a natural glycoside which foams in water and serves as a natural detergent.

Sarsaparilla Root (*Smilax utilis*) is a mild, natural detergent and skin purifier that contains saponins.

*Sclerotium* Gum is a natural polysaccharide obtained through fermentation of a sugar based medium by the yeast, *Sclerotium*.

Sea Buckthorn Oil (*Hippophae rhamnoides*) is a rich source of antioxidant vitamins E and A. It is high in essential fatty acids, particularly rare palmitoleic acid, a constituent of the skin's sebum.

Sea Herbal Complex is a special blend of sea herbals such as bladderwrack and *laminaria*, frequently used in skin care products.

Sea Salt is a mineral-rich salt from sea water used in bath soaks and body scrubs as a skin softener.

Sea Ware or Seaweed Extracts is a blend of herbal sea extracts, typically consisting of variations of: bladderwrack, carrageenan (seaweed gum), iodides and *laminaria*.

Selenium is an antioxidizing micronutrient mineral that has a strong soothing effect and is helpful in removing buildup.

Sericite Mica is a transparent mineral used to provide slip and light absorption in cosmetics.

Sesame Oil (*Sesamum indicum*) is a rich emollient, high in linoleic and oleic fatty acids, frequently used as a carrying agent for other ingredients in cosmetic formulations.

Shea Butter (*Butyrospermum parkii*), also Karite Butter, is a moisture-rich butter and a superb emollient that is high in fatty acids and other nutrients. It is a common ingredient in skin moisturizers and sun care products.

Siberian Pine Needle Oil (*Pinus sylvestris*), also known as Fir Oil, is an aromatic essential oil that serves as an antimicrobial and skin purifier, and which possesses a pleasant fragrance.

Silica is a mineral used in cosmetic products as a thickener, stabilizer, and promoter of sunscreen efficacy.

Silk Powder is used in makeup powders to even out and smoothen skin tone and contains high amounts of amino acids and Vitamin E.

Skullcap (*Scutellaria baicalensis*) is a mild tonic and stimulant with antioxidant and antimicrobial properties.

Sobitan Olivate and Cetearyl Olivate are non-ionic, non-ethoxylated, PEG-free, emulsifiers derived from olive oil. They can be used to reduce skin water loss, and have a desirable moisturizing effect. Sobitan Olivate and Cetearyl Olivate are hypoallergenic and biomimics the skin.

Sodium Cocoate (*Cocos nucifera*), also known as Coconut oil, is saponified with an alkaline salt and serves as a lathering agent in soaps.

Sodium Hyaluronate is a naturally occurring polysaccharide used in skin care preparations to helps attract and retain moisture (humectant).

Sodium Hydroxide is an alkaline salt that is used in small amounts in cosmetics as a pH modulator and cleansing agent.

Sodium Palmitate (*Elaesis guineensis*), also known as palm oil, may be saponified with an alkaline salt and is known primarily for its role in the hardness and durability of bar soaps.

Sodium PCA is a salt of the amino acid, glutamic acid, which can act as a humectant to help attract and retain moisture to the skin.

Sorbitol is a white, crystalline alcohol used as a moisturizing agent and sugar substitute.

Soy Lecithin is an excellent source of protein and Vitamin B that helps revitalize skin.

Soybean Oil (*Glycine soya*) is an effective emollient, high in linoleic, oleic, palmitic and linolenic acids, promoters of healthy skin.

Soy Protein is derived from the soybean and is used as a source of protein.

Spearmint Oil (*Mentha spicata*) is an essential oil used for its stimulating and tonic properties and refreshing fragrance.

Squalane is often added to cosmetics for its emollient and antibacterial properties. Often, olive oil squalane is the preferred squalane, as it is the most stable and compatible with the skin.

St. John's Wort (*Hypericum perforatum*), in its oil form, is an excellent emollient and skin softener used in sun and skin care products for its healing properties and effects on dry, irritated skin.

*Stevia* Extract is a natural sweetener, with far greater sweetening potential than sugar.

Sucrose is a derivative of cane sugar that hydrates and encourages moisture retention in the skin.

Sugar-Cane Ethanol is a by-product of organic sugar production which serves as a solvent for organic herbal extracts.

Sunflower Oil (*Helianthus annus*) is an extract from sunflower seeds that serves as a rich emollient high in linoleic and oleic essential fatty acids, allowing it to serve as a good base for massage oils and lotions.

Sweet Almond Oil (*Amigdalus communis*, var. *dulcis*) is an excellent emollient high in oleic, linoleic and other fatty acids, and is ideal in the treatment of very dry skin on account of its soothing and moisturizing effects.

Sweet Orange Oil (*Citrus sinensis*) is a pleasant-smelling essential oil from the peel of sweet oranges which has anti-inflammatory, antibacterial, antifungal, and refreshing properties and contains flavonoids and vitamins A, B, C and E.

Sweet Fennel is a pure essential oil of crushed Fennel seeds which increases the elasticity of the connective tissues of the skin and anti-wrinkle, anti-aging, and tightening effects on the skin.

Sweet Orange is a pure essential oil from the peel of ripe oranges and has astringent, antibacterial, antiseptic, toning and cleansing properties.

Tea Tree Oil (*Melaleuca alternifolia*) is an essential oil with powerful antiseptic and germicidal properties, used in small amounts in cosmetics, such as therapeutic masks, moisturizers, and acne treatments.

Thyme Extract is an antimicrobial, astringent and expectorant with a mild soothing effect.

Titanium Dioxide is a naturally occurring mineral that offers significant protection from damaging UVA/UVB rays, thus serving as a superb ingredient for sunblocks.

Tofu is derived from soybeans and is rich in protein, calcium, B vitamins and other nutrients beneficial to the skin.

Vanilla Extract is warming and soothing to the skin and has a pleasant fragrance.

Vegetable Glycerin is a rich humectant, emollient and lubricant extracted from vegetable oils, often used in cosmetic formulations.

Vegetable Protein is a leading source of vitamins and essential amino acids that, when applied topically, serves as an excellent hydrator which is readily absorbed by the skin to improve texture.

Vetiver (*Vetiveria zizanoides*) is a soothing essential oil used in cosmetics for its smoky, earthy scent and natural sedative properties.

Violet (*Viola odorata*) is an analgesic and soothing agent containing salicylic acid that is beneficial to sensitive skin. In combination with other oils and extracts, it is often used as a fragrance.

Vitamin A is an antioxidant vitamin serving as a natural preservative in cosmetics and widely used to treat many skin conditions, as it promotes the formation of new skin cells as well as helps regulate oil secretion in the sebaceous glands. Vitamin A is very beneficial for dry or sun-exposed skin, as its antioxidant, soothing, anti-aging and hydrating properties make it a frequent component of sun protection creams.

Vitamin B-complex (Herbal) is a set of water-soluble vitamins that, when applied topically, help control excess oil secretion. They are especially effective in preparations for rough skin and blemishes and as a promoter of skin cell respiration. Calcium D-pantothenate and inositol are the two B-complex vitamins most beneficial to skin health.

Vitamin C is a powerful antioxidant and nutrient that is beneficial to the skin, as it plays an essential role in building collagen, a large and crucial component of our skin. Additionally, Vitamin C is a natural preservative that protects both the oil and water phases of cosmetics.

Vitamin E (d-Alpha Tocopherol) is a very strong antioxidant which protects the skin from free radicals and aids in proper utilization of oxygen in the tissues. In cosmetics, Vitamin E also serves as a natural preservative, which protects the oil phase in creams and lotions.

Vitamin F is a skin protector and revitalizer consisting of linoleic and linolenic acids, two essential fatty acids. It is very frequently used in moisturizers, as it helps soothe rough, dry, or chapped skin.

Together, Vitamins A, C and E and citrus seed extract serve as an excellent natural preservative.

Walnut Extract (*Juglans nigra*) is a tonic and astringent beneficial to the skin, which may also be used as a source of brown coloring.

Walnut Shells (*Juglans nigra*) are natural exfoliants used in facial masks which help break up oil deposits and clear away dead skin cells and debris.

Watercress (*Nasturtium officinale*) is a good source of vitamins A, B-complex and C and has soothing and conditioning properties which are very beneficial to the skin.

Wattle seed (*Acacia vitoriae*) is an extract used to make syrup containing anti-inflammatory properties.

Wheat Germ Oil (*Triticum vulgare*) is an anti-inflammatory and skin nourisher that, because of its high vitamin E content, also acts as a natural preservative.

Wheat Grass (*Triticum vulgare*) is an anti-inflammatory containing plant sterols which is often used in the treatment of eczema and dermatitis.

Wheat Protein (*Triticum vulgare*) is a water-soluble protein derived from wheat that, when applied topically, helps retain skin moisture, thereby minimizing fine lines and wrinkles.

White Birch Extract (*Betula alba*) is a soothing and purifying agent for the skin that serves as a good addition to sun care products and face creams.

White *Camellia* Oil (*Camellia japonica*) is a rich oil from the white *camellia* flower skin care formulations as an excellent moisturizer, antioxidant, and nutrient for the skin.

White Pine Bark (*Pinus strobus*) is a soothing extract used in preparations for treating dry skin.

Wild Ginger Root (*Asarum canadense*), also known as Nigerian Root, is added to bath products and massage lotions to warm and soothe muscles and skin. In small amount, it may also be used as a fragrance.

Wintergreen Oil (*Gaultheria procumbens*) is an aromatic tonic, stimulant, and freshener, which has a warming effect on the skin. It is a frequent component of various body rubs and bath oils and contains a high concentration of salicylic acid.

Witch Hazel (*Hamamelis virginiana*) is a natural astringent, anti-irritant, anti-inflammatory, and tonic, and is frequently used in facial cleansers, toners and lotions.

Xantham Gum is a gum which serves as a non-toxic thickener and stabilizer for many compounds, including those in cosmetics.

Xylitol is a sugar alcohol from the birch tree, and may be used as a sweetener.

Yarrow (*Achillea millefolium*) is a known anti-inflammatory and anti-irritant and helps in firming the skin.

Yeast is has a high concentration of protein and B vitamins and is a good cosmetic additive on account of its nutritional properties.

Yellow Dock Extract is an astringent and antibacterial that helps restore and purify skin.

Ylang Ylang Oil (*Cananga odorata*) helps balance sebum production and revitalize, soothe, and balance dry, oily or combination skin. It also possesses a pleasant floral scent.

Yucca Root (*Yucca schidigera*) is a detergent used in soaps for its foaming and purifying abilities and presence of saponins.

Zinc is a mineral which aids in skin cell regeneration and cellular healing.

Zinc Oxide, sometimes zincite, is a water-insoluble substance that may also serve as an effective sunblock.

These and other ingredients may be implemented into the various components of a skin treatment composition in accordance with the present invention, further including other ingredients and medications not mentioned above, such as over the counter medications classified as skin protectants. For example, and without deviating from the scope of the present invention, one or more of the additives mentioned above (including over the counter products) may be incorporated into the one or more of: the cleansing solution, the silicone component, or the mineral powder component.

Moving on to a discussion of the figures, including discussion of various methods for preparing and applying a skin treatment in accordance with the present invention, the following discussion addresses a number of embodiments and applications of the present invention, in which is shown by way of illustration specific embodiments in which the invention may be practiced. It is to be understood that other embodiments may be utilized and changes may be made without departing from the scope of the present invention.

Figure 1B:
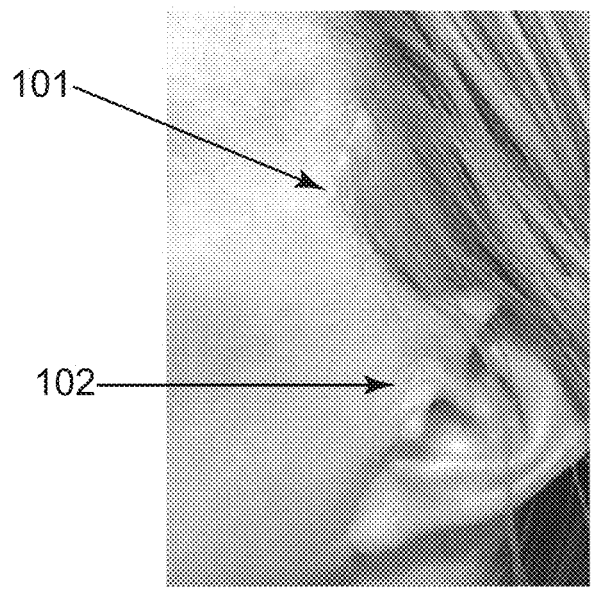
Figure 2A:
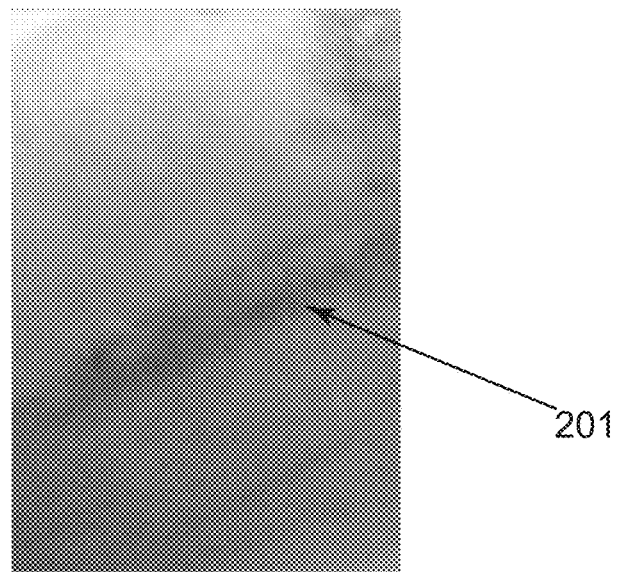
FIG. 2(a)-(b) depicts a photograph of a non-treated breast-lift scar (a) and an after-treatment photograph (b) of the same skin area having been treated (during a 1-month period) with a composition in accordance with the present invention.
Figure 2B:
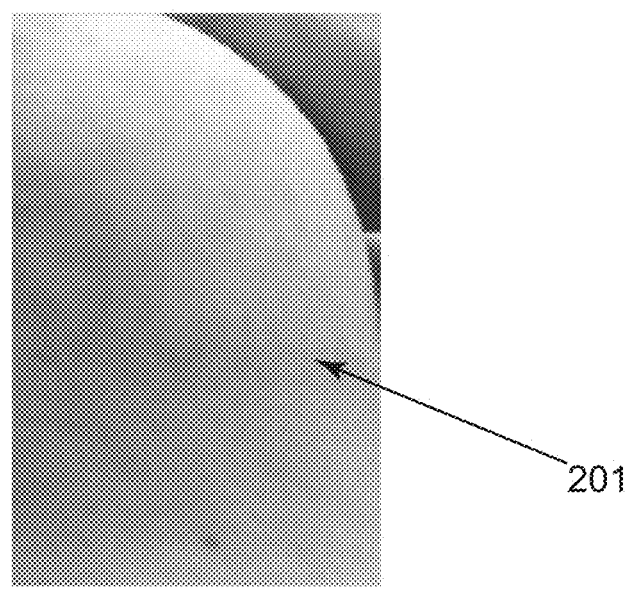

Turning to the first three figures: FIG. 1(*a*)-(*b*) depicts before (FIG. 1 (*a*)) and after (FIG. 1 (*b*)) photographs of a patient treated with a composition in accordance with the present invention; FIG. 2(*a*)-(*b*) depicts a photograph of a non-treated breast-lift scar (FIG. 2 (*a*)) and an after-treatment photograph (FIG. 2 (*b*)) of the same location having been treated throughout a 1-month period; and similarly, FIG. 3(*a*)-(*b*) depicts photographs of a patient treated with a composition in accordance with the present invention, and another that was treated with silicone tape.

Figure 3A:
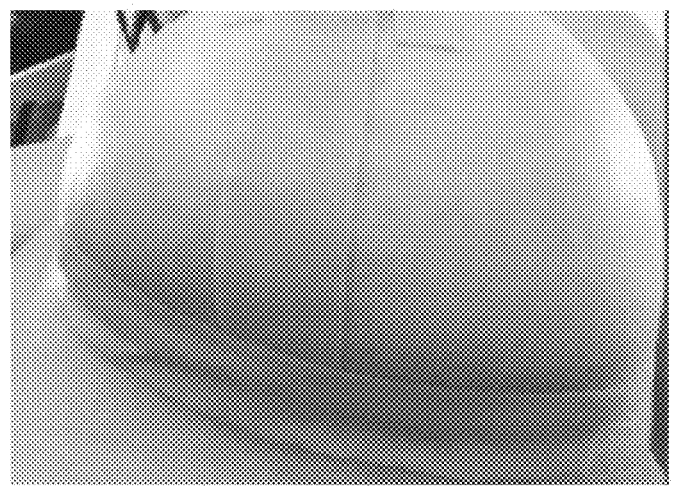
FIG. 3(a)-(b) depicts photographs of a patient treated with a composition in accordance with the present invention, and another that was treated with silicone tape.
Figure 3B:

In each of these cases a cleansing solution was applied topically, followed by a silicone elastomer mixture for treating the skin FIG. 1(*a*)-(*b*) shows two regions of a scar, region 101 and 102, along the hairline and ear of the patient. As is shown, the progress is significant with the scarred skin on region 102 almost unnoticeable. More drastically, FIG. 2(*a*)-(*b*) shows region 201 of a patient's breast after undergoing a breast-lift procedure. That scarred skin is significantly improved as the scar was virtually undetectable after a single month of treatment. Finally, the scarred region of other another patient's breast after going through a similar breast-lift procedure, is shown with FIG. 3(*a*) showing a patient that was treated with silicone tape, and FIG. 3(*b*) showing a patient that was treated with a skin treatment in accordance with the present invention. FIG. 3(*b*) illustrates how the silicone component of a composition in accordance with the present invention may act as a more comfortable and practical alternative to other solutions.

Figure 4:
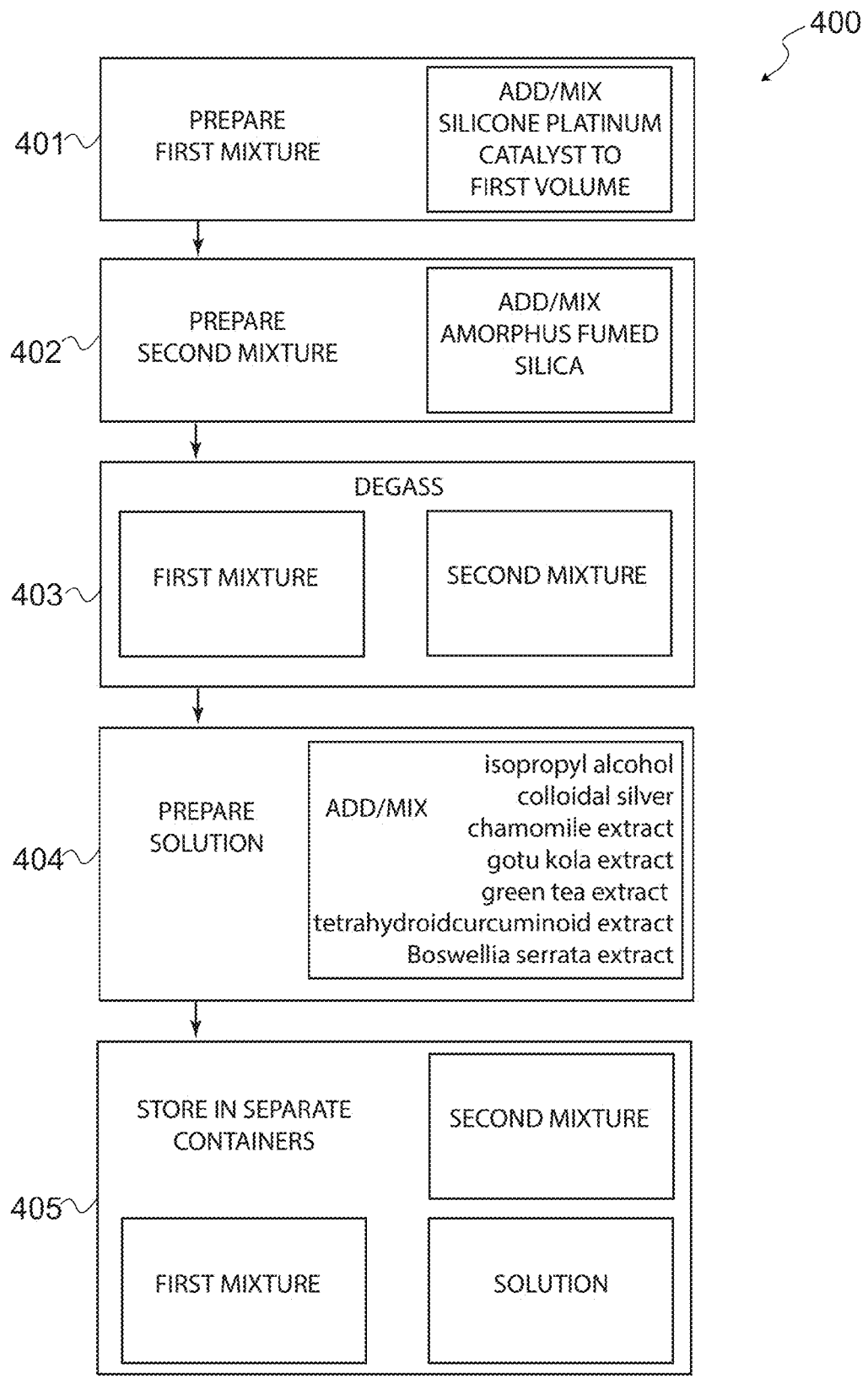
FIG. 4 depicts a flowchart illustrating a method for preparation of a skin treatment in accordance with one embodiment of the present invention.

Turning to the next figure, FIG. 4 depicts a flowchart illustrating a method for preparation of a skin treatment in accordance with one embodiment of the present invention. More specifically, FIG. 4 shows method 400, which may be practiced in order to prepare a cleansing solution and one or more silicone mixtures. Using method 400, one or more of the above mentioned components or layers of the composition may be prepared in order to create a skin treatment to treat scars, including keloids, burns, or wrinkles on the skin. It should be noted that the steps described in relation to method 400 may be taken in the given sequence or any conceivable sequence without limiting the scope of the present invention.

Generally, beginning with step 401, one or more silicone elastomer mixtures may be prepared for the silicone component or layer of the skin treatment. In one embodiment, step 401 comprises of preparing a first mixture by adding and mixing a silicone platinum catalyst to a first volume of a silicone elastomer. The resulting amount of silicone platinum catalyst may be between 0.03% to 0.09% by wt. of the first mixture. In another embodiment, step 401 may comprise of adding and mixing a silicone platinum catalyst to a first volume of a silicone elastomer, wherein the silicone platinum catalyst is added to the first volume of the silicone elastomer in the proportion of 1 to 2 grams of the silicone platinum catalyst per kilogram of the first volume of the silicone elastomer.

In step 402, a second mixture may be prepared, which contains a silicone elastomer and closely resembles the first mixture. In one embodiment, step 402 comprises of preparing a second mixture by adding and mixing amorphous fumed silica to a second volume of the same silicone elastomer. The resulting amount of amorphous fumed silica may be between 0.49% to 0.98% by wt. of fumed silica, similar to the first mixture. Additionally, a methylhydride crosslinker may be added to the second mixture, so that the second mixture includes no more than 10% by wt. of the methylhydride crosslinker. Furthermore, both the first volume of the silicone elastomer and the second volume of the silicone elastomer should be equal volumes so as to facilitate the correct proportions of the added ingredients. Nevertheless, different volumes may be implemented into a method so long as the proportions of the added ingredients are maintained. Furthermore, other ingredients may be added in steps 401 and 402 to both the first mixture and second mixture.

For example, and without limiting the scope of the present invention, steps 401 and 402 may further comprise of adding and mixing amorphous fumed silica to the first mixture, wherein the amorphous fumed silica is added to the first mixture so the resulting amount of amorphous fumed silica is between 0.49% to 0.98% by wt. of the first mixture. Steps 401 and 402 may further comprise adding and mixing 0.25-0.49% by wt. of a cyclopentasiloxane to the first mixture, and adding and mixing 0.25-0.49% by wt. of a cyclopentasiloxane to the second mixture; Steps 401 and 402 may further comprise adding and mixing 0.18-0.49% by wt. of a hydroxyl terminated polymethylphenylsiloxane to the first mixture, and adding and mixing 0.18-0.49% by wt. of a hydroxyl terminated polymethylphenylsiloxane to the second mixture. Steps 401 and 402 may further comprise adding and mixing 0.49-0.98% by wt. of a dimethicone to the first mixture, and adding and mixing 0.49-0.98% by wt. of a dimethicone to the second mixture.

Alternatively, in another embodiment, step 402 may comprise of adding and mixing amorphous fumed silica, wherein the amorphous fumed silica is added to the second volume of the silicone elastomer so the resulting concentration of amorphous fumed silica is 0.0015 g/mL. In this embodiment, additional ingredients may be implemented with the silicone elastomer mixtures by adding and mixing gotu kola extract, chamomile extract, green tea extract, and tetrahydrocurcuminoid to either the first or second silicone elastomer mixtures. A discussion of this later approach is discussed below with reference to FIG. 5. Note that in either embodiment the first volume of the silicone elastomer and the second volume of the silicone elastomer are substantially equal volumes.

In step 403 both the first and second mixtures may be degassed. Degasification may be implemented in order to remove any dissolved gases from the solutions. Degassing the first and second mixtures is preferably performed for a period of at least five to twenty minutes although other times may be implemented, and there are numerous possible methods for degassing the first and second mixtures, any of which may be implemented without deviating from the scope of the present invention.

In step 404 the cleansing solution may be prepared. Note however that this step may be performed before step 401 or at any other time without deviating from the scope of the present invention. When preparing the solution for mixing with the first and second mixtures or silicone elastomers, the following ingredients with the following concentrations may be mixed together: 0.5-3% by wt. of isopropyl alcohol, 73-90% by wt. of colloidal silver, 1-5% by wt. of chamomile extract, 1-5% by wt. of gotu kola extract, 1-5% by wt. of green tea extract, 1-4% by wt. of a curcuminoid such as tetrahydrocurcuminoid, and 1-5% by wt. of *Boswellia serrata* extract. Of course, other ingredients may be added or substituted without deviating from the scope of the present invention, and alternate ranges and concentrations may be possible. Furthermore, the ingredients of the solution may depend, for example, on the ingredients chosen for the first and second mixtures of silicone elastomers. For example, and without limiting the scope of the present invention, in an embodiment in which the first and second mixtures do not contain *Boswellia serrata* extract, it may be desirable to include this ingredient in the solution. Alternatively, in embodiments in which the first or second mixtures do contain *Boswellia serrata* extract, it may be desirable to exclude that ingredient from the solution.

In step 405, the first mixture, the second mixture, and the solution may be stored in separate vessels for at least a 24 hour period until ready. At this point, the solution and mixtures are ready for application, which will be discussed below with reference to FIG. 6 and FIG. 7.

Figure 5:
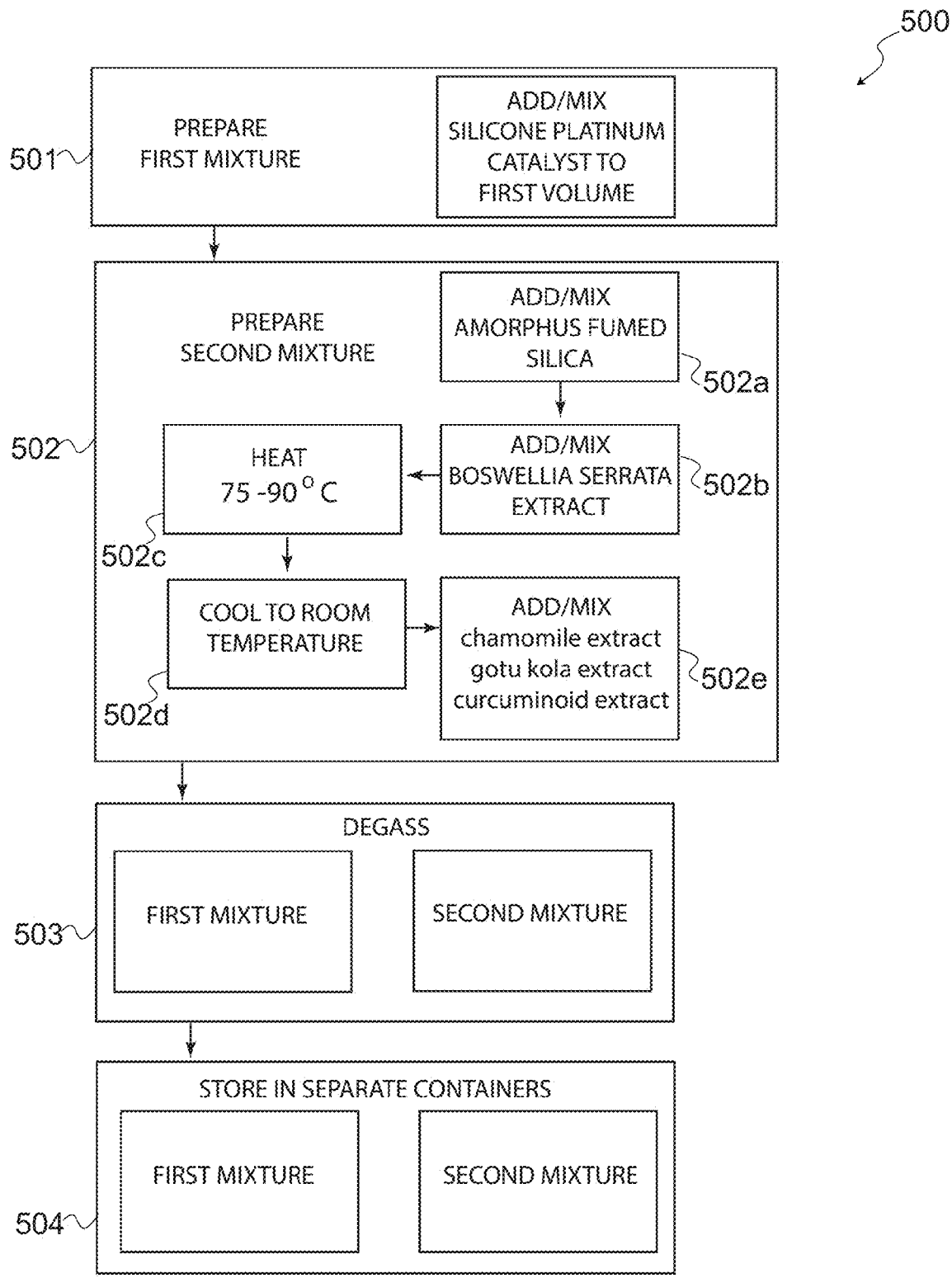
FIG. 5 depicts a flowchart illustrating another method for preparation of a skin treatment in accordance with one embodiment of the present invention.

Turning now to the next figure, FIG. 5 depicts a flowchart illustrating another method for preparation of a skin treatment in accordance with one embodiment of the present invention. More specifically, FIG. 5 shows method 500, which may be practiced in order to prepare a first silicone mixture and a second silicone mixture having additives or ingredients similar to the cleansing solution discussed above. Using method 500, one or more of the above mentioned components may be prepared in order to create a skin treatment to treat scars, including keloids, burns, or wrinkles on the skin. It should be noted that the steps described in relation to method 500 may be taken in the given sequence or any conceivable sequence without limiting the scope of the present invention.

Generally, beginning with step 501, one or more silicone elastomer mixtures may be prepared for the silicone component of the skin treatment. In one embodiment, step 501 comprises of preparing a first mixture by adding and mixing a silicone platinum catalyst to a first volume of a silicone elastomer. The resulting amount of silicone platinum catalyst may be between 0.03% to 0.09% by wt. of the first mixture. In another embodiment, step 501 may comprise of adding and mixing a silicone platinum catalyst to a first volume of a silicone elastomer, wherein the silicone platinum catalyst is added to the first volume of the silicone elastomer in the proportion of 1 to 2 grams of the silicone platinum catalyst per kilogram of the first volume of the silicone elastomer. For example, to 20 milliliters (mL or cc's) of a first volume of a commercially available silicone elastomer, a silicone platinum catalyst in the amount of 1 to 2 grams (g) of catalyst per kilogram (kg) may be added. The added silicone platinum catalyst may be mixed into the 20 mL of the first volume. This step may be identical to step 401 discussed above. However, since method 500 incorporates various ingredients from the cleansing solution into the silicone elastomer mixtures, step 502 may involve additional or alternate steps in order to better infuse those ingredients with the silicone elastomer.

In step 502, a second mixture is prepared by following the following series of steps: in step 502*a* and 502*b*, amorphous fumed silica and *Boswellia serrata* extract may be added and mixed to a second volume of the silicone elastomer, respectively. The amorphous fumed silica may be added to the second volume of the silicone elastomer so the resulting concentration of amorphous fumed silica is 0.0015 g/mL. Furthermore, the *Boswellia serrata* extract may be added to the second volume of the silicone elastomer so the resulting concentration of *Boswellia serrata* extract is 0.005 g/mL. Note that the second volume of the silicone elastomer and the first volume of the silicone elastomer should have equal volumes. In step 502*c*, the resulting mixture of steps 502*a* and 502*b* may be heated to a range of 75 to 90 degrees Celsius, while mixing. In step 502*d*, the resulting mixture of step 502*c* may be cooled to room temperature. In an exemplary embodiment, it is desirable to perform the mixing and heating of these ingredients using a glass-lined vessel such as a glass beaker. Once cooled, in step 502*e*, ingredients including gotu kola extract, chamomile extract, green tea extract, and a curcuminoid extract may be added and mixed. In one embodiment, these ingredients may be added so that their concentration is as follows: 0.0075 g/mL of gotu kola extract, 0.0075 g/mL of chamomile extract, 0.0075 g/mL of green tea extract, and 0.0025 g/mL of a curcuminoid extract such as a tetrahydrocurcuminoid extract. Additionally, note that while the above example requires two equal 20 mL volumes of the silicone elastomer, other volumes may be utilized as long as each of the two parts are substantially equal with respect to each other on a volume basis. For example, larger or smaller batches may be compounded and stored per the above steps.

In step 503, both the first and second mixtures may be degassed. As with step 403 above, degasification may be implemented in order to remove any dissolved gases from the solutions and the first and second mixtures may be degassed for a period of at least five to twenty minutes. Of course, other times may be implemented, and there are numerous possible methods for degassing the first and second mixtures, any of which may be implemented without deviating from the scope of the present invention.

In step 504, the first mixture and the second mixture may be stored in separate vessels for at least a 24 hour period until ready. After that period, the mixtures are ready for application, which will be discussed below with reference to FIG. 6 and FIG. 7.

Figure 6:
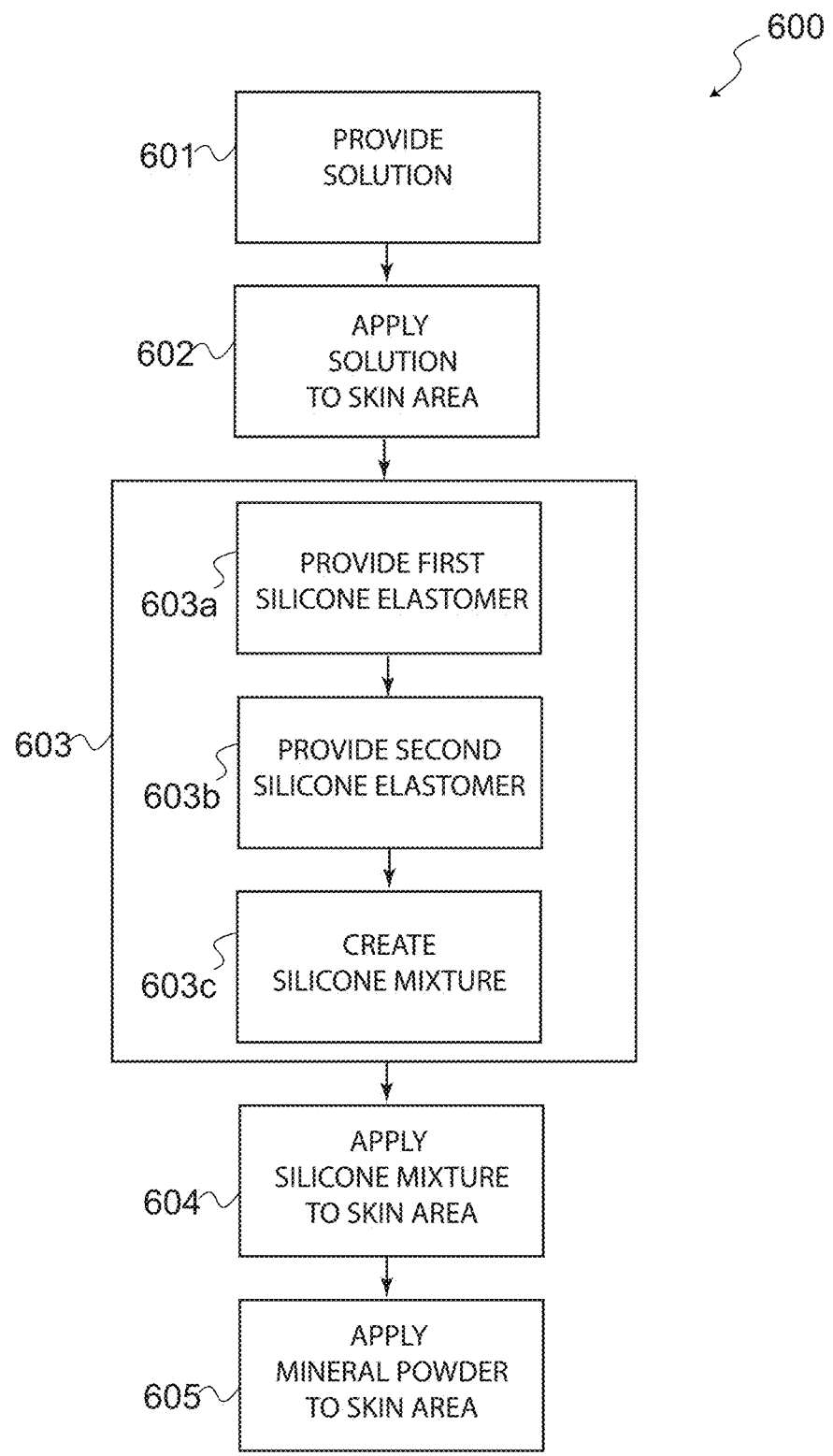
FIG. 6 depicts a flowchart illustrating a method for applying a skin treatment in accordance with one embodiment of the present invention, wherein the method may be used to treat a scar or burns on a patient's skin.

Now turning to the next figure, FIG. 6 depicts a flowchart illustrating a method for applying a skin treatment in accordance with one embodiment of the present invention, wherein the method may be used to treat a scar or burns on a patient's skin. More specifically, method 600 is shown, illustrating a method of application or administration of one embodiment of the present invention, wherein a cleansing solution, a plurality of silicone elastomer mixtures, and a mineral powder are utilized and applied to a patient's skin in order to treat and camouflage damaged skin area. At least one component of the treatment, for example the silicone component, may be used as a liquid band-aid, to treat burns or scars, or to treat more serious wounds such as gun-shot wounds. It should be noted that the steps described in relation to method 600 may be taken in the given sequence or any conceivable sequence without limiting the scope of the present invention.

In step 601, a first solution including a cleansing solution for treating a skin area may be provided. The cleansing solution may include a mixture of 0.5-3% by wt. of isopropyl alcohol, 73-90% by wt. of colloidal silver, 1-5% by wt. of chamomile extract, and 1-5% by wt. of gotu kola extract. Additionally, the cleansing solution may also include 1-5% by wt. of green tea extract, 1-4% by wt. of a curcuminoid such as tetrahydrocurcuminoid, and 1-5% by wt. of *Boswellia serrata* extract. Of course, other additives and ingredients may be implemented with the cleansing solution without limiting or deviating from the scope of the present invention.

In step 602 the cleansing solution may be applied to the skin area affected by a scar or burn. In step 603, a silicone mixture may be provided. In the shown embodiment, the following steps may be taken in order to provide the silicone mixture:

In step 603a, a first silicone elastomer is provided for mixing with a second silicone elastomer. The first silicone elastomer typically includes a combination of the following: polydimethylsiloxane, dimethyl methylhydrogen siloxane copolymer, a noncrystalline silicone dioxide, a platinum catalyst, and hydroxyl terminated polymethylphenylsiloxane. Of course, the first silicone elastomer may include other ingredients such as fumed silica, and cyclopentasiloxane.

In step 602b, a second silicone elastomer is provided for mixing with the first silicone elastomer. The second silicone elastomer typically comprises similar ingredients although a platinum catalyst may be absent from the second silicone elastomer mixture and includes instead a methylhydride crosslinker.

In step 603c, equal volumes of the first and second silicone elastomers are mixed into a silicone mixture, and the silicone elastomer mixture may be allowed to cure for a predetermined period of time. In one embodiment, the dispensed volumes may be mixed for substantially 60 seconds. Mixing may be accomplished with a finger, brush, or other tool known in the art. The resulting mixture may already be curing, but may not be completely cured at the 60-second mark. Other times may be implemented depending on the total volume of the mixture—for example slightly longer times may be required for larger volumes. In exemplary embodiments, substantially equal volumes of the first mixture and second mixture may be dispensed such that when the volumes are spread out over a scar or desired area, the scar or desired area is covered. In other exemplary embodiments, equal volumes may be dispensed on a surface prior to application on the skin, such as onto an intermediary substrate. In yet other embodiments, a dual syringe or two separate syringes may be implemented, wherein each syringe contains each separate silicone elastomer to be mixed into the silicone mixture.

In step 604, the mixture may be applied on the skin area treated with the cleansing solution.

In step 605, after allowing the mixture to stand on the treated skin area, the mineral powder component may be applied to camouflage the scarring or burned skin. In addition to helping conceal the affected skin area, the mineral powder may contain, as mentioned above, ingredients that help the healing process. For example, the mineral powder may provide UV protection. In an exemplary embodiment, to uniquely speed the cure time once the mineral powder is added, the mineral powder composition utilized to accelerate cure times may contain amorphous fumed silica and the sunscreen ingredients as discussed above.

After application of the three components, a user should then wait between a minimum of five minutes to about ten minutes for the resulting composition on the skin to sufficiently cure. This waiting period enables the user to be able to immerse the resulting composition in water without the immersion disturbing the composition. That is, after a user has waited for a minimum of five minutes after applying an exemplary mineral powder component to the applied solution and silicone mixture, a user may swim or bathe without the resulting silicone-based elastomer layer being disturbed.

Figure 7:
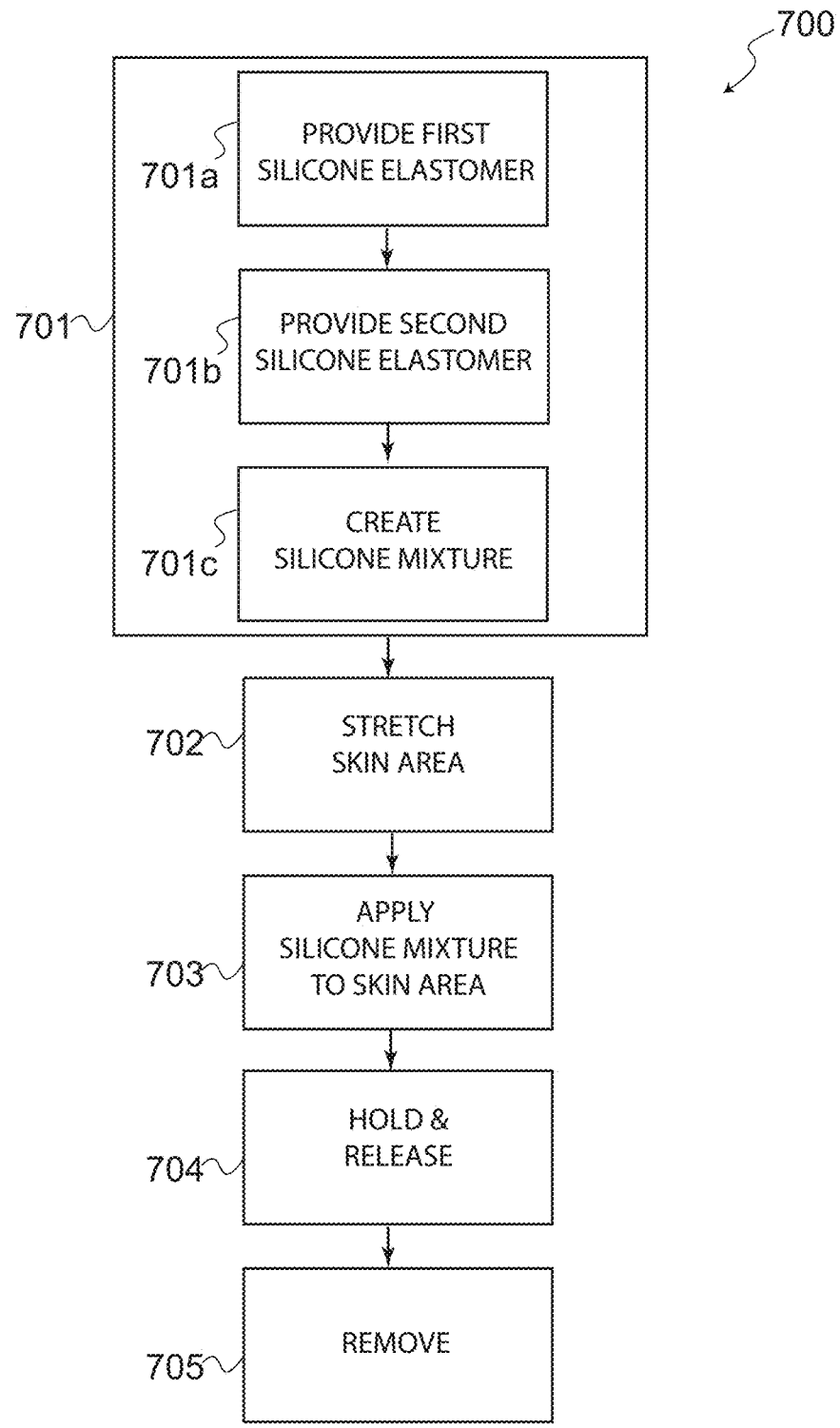
FIG. 7 depicts a flowchart illustrating another method for applying a skin treatment in accordance with one embodiment of the present invention, wherein the method may be used to treat wrinkles on a patient's skin.
Figure 8:
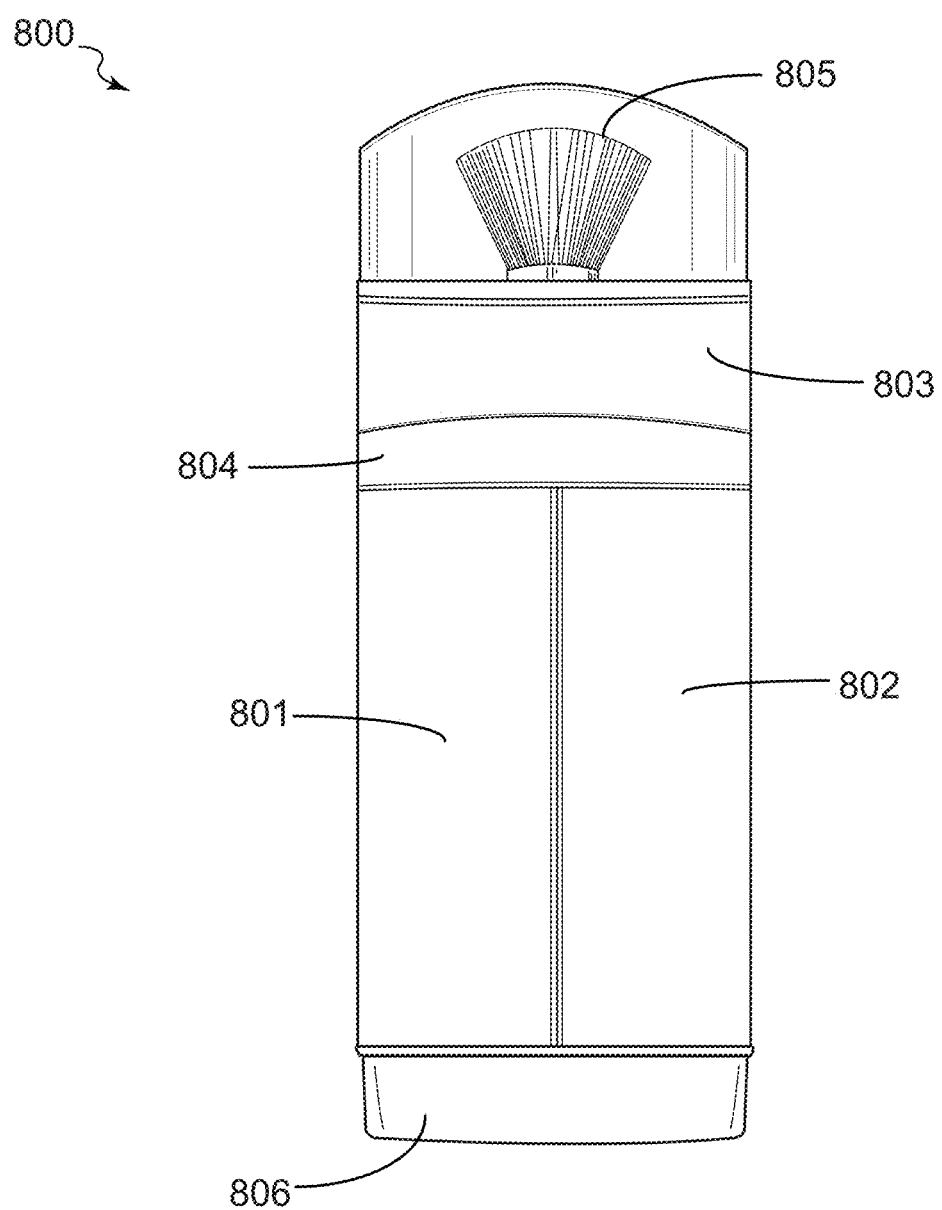
FIG. 8 depicts an exemplary embodiment of a device or applicator, in accordance with the present invention, the applicator for storing and dispensing different compositions of the skin treatment.

Turning to the next figure, FIG. 7 depicts a flowchart illustrating another method for applying a skin treatment in accordance with one embodiment of the present invention, wherein the method may be used to treat wrinkles on a patient's skin. More specifically, method 700 is shown, illustrating a method of application or administration of one embodiment of the present invention, wherein a silicone elastomer mixture is applied to a patient's skin in order to alleviate or eradicate wrinkles.

An exemplary embodiment of the present invention may be used to smooth wrinkles out by holding the wrinkle apart, moisturizing the area, heating the wrinkle and allowing for synergistic use of any anti-aging topical products such as Retin-A®, vitamin C, and other anti-aging agents and additives mentioned above, to act on the affected area. As is explained below, onset of action is typically between thirty minutes at the least to about twelve hours at the most. In some applications, a patient may apply the silicone mixture prior to a big event for half an hour and achieve a smoothing of their wrinkles. In other applications, the patient may apply the silicone mixture prior to going to bed leaving it on while sleeping and removing in the morning To remove the wrinkles in their entirety, the silicone mixture may be applied nightly until the patient or user achieves the desired result. Desired result may be achieved in 12 hours to one week. Once a smoothing effect has been achieved, application may be reduced to three times a week. In one embodiment, the silicone mixture is non-irritating, non-toxic, and odorless. Typically, the mixture functions by relaxing the wrinkled skin and preventing the creasing of the wrinkle over a period of time. In this manner, the silicone mixture may prolong the effects of any type of Botulinum Toxin Type A, Botox, Xeomin, Dysport, etc., which may be helpful when a user or patient is using the present skin treatment in addition to other procedures known in the art. It should be noted that the steps described in relation to method 700 may be taken in the given sequence or any conceivable sequence without limiting the scope of the present invention.

In step 701 a silicone elastomer mixture is provided. This step may be similar to step 603, as administration to a desired skin area affected by undesirable wrinkles is identical to that of a scarred or burned skin. Hence, step 701 may comprise of the following steps in order to provide the silicone mixture:

In step 701*a*, a first silicone elastomer may be provided for mixing with a second silicone elastomer. The first silicone elastomer typically includes polydimethylsiloxane, a noncrystalline silicone dioxide, a platinum catalyst, and hydroxyl terminated polymethylphenylsiloxane. Of course, the first silicone elastomer may include other ingredients such as fumed silica and cyclopentasiloxane.

In step 701*b*, a second silicone elastomer may be provided for mixing with the first silicone elastomer. The second silicone elastomer typically comprises similar ingredients although a platinum catalyst may be absent from the second silicone elastomer mixture and includes instead a methylhydride crosslinker.

In step 701*c*, equal volumes of the first and second silicone elastomers are mixed into a silicone mixture, and the silicone elastomer mixture may be allowed to cure for a predetermined period of time. In one embodiment, the dispensed volumes may be mixed for substantially 5-10 seconds. Mixing may be accomplished with a finger, brush, or other tool known in the art. In exemplary embodiments, equal volumes may be dispensed on a surface prior to application on the skin, such as onto an intermediary substrate. In other embodiments, a dual syringe or two separate syringes may be implemented, wherein each syringe contains each separate silicone elastomer to be mixed into the silicone mixture. Once the silicone mixture is mixed for 5-10 seconds, the mixture may be applied.

In step 702, prior to applying the silicone mixture, the area of the skin with wrinkles may be stretched so as to smoothen the wrinkled skin area. That is, the desired wrinkle or wrinkles may be stretched out by one hand to the point of complete relaxation of the skin.

In step 703, the application of the silicone mixture may be achieved in any number of ways. For example, application may include using a double syringe that directly applies the mixture onto the skin over the wrinkle or wrinkles. In other embodiments, as mentioned above, the mixture may be created on a separate surface and then applied to the desired wrinkled skin. Once the mixture is on the desired skin area, the silicone mixture may be spread beyond the border of the desired skin area by about 5 mm.

In step 704, the wrinkle, or wrinkles may be held apart for a period of three minutes before releasing the skin—this allows the composition to harden and the treatment of the skin to begin. It is typically desirable for the patient to prevent from touching the application or get it wet for the first 10 min.

Finally, in step 705, once a desired period of application has passed—anywhere between thirty minutes to twelve hours—the silicone mixture may be removed. Typically, removal may achieved by gently pulling up on a hardened corner of the application and pulling the dried silicone film off in one piece.

Again, depending on the skin area to be treated, the silicone mixture may be applied with more or less frequency. Once a smoothing effect has been achieved, application may be reduced. Furthermore, the steps described above may be practice in similar or different sequences without deviating from the scope of the present invention.

Turning now to the last figure, FIG. 8 depicts an exemplary embodiment of a device or applicator in accordance with the present invention, the applicator for storing and dispensing different compositions of the skin treatment. In the embodiment shown, applicator 800 is a multi-chambered container for storing different components of a skin treatment. Applicator 800 contains three chambers: chamber 801, chamber 802, and chamber 803. Each of the three chambers maintains its composition physically and chemically separate from the compositions within the other chambers, until the contents are dispensed. In an exemplary embodiment, chamber 801 and chamber 802 may each hold a silicone elastomer as described above, wherein mixing of the two silicone elastomers may be accomplished by rotating an activator component 806 of applicator 800. In this embodiment, the contents of chambers 801 and 802 may be dispensed simultaneously thereby creating the desired silicone mixture. Chamber 803 may contain a mineral powder, which may be applied using an integrated brush 805. Chamber 803 may dislodge from applicator 800's body revealing dispenser section 804, which contains an opening (not shown) for dispensing the silicone mixture. As mentioned above, other devices including double syringes or single syringes may be used to dispense or contain the various components of a skin treatment in accordance with the present invention.

Of course the skin treatment described in this disclosure may be packaged in a single container or device such as applicator 800 or in different and distinct containers all packaged as a unit to provide users a kit. In an exemplary embodiment, a kit or packaging for providing a skin treatment may include a first container including two compartments for separately storing silicone elastomers (one with the catalyst and the other with a cross linker) in order to prevent the silicone mixture from curing prior to application. Furthermore, the packaging may include a second container comprising the cleansing solution for a user to apply the first layer of the treatment prior to the silicone mixture. Yet another container may be provided in the packaging, which includes the mineral powder or setting powder for the user to apply the camouflage layer of the treatment. Still, other forms of packaging and storing for the skin treatment may be provided, which are known in the art, without deviating from the scope of the present invention.

As a final point on the uses of the presently disclosed skin treatment, the disclosed skin treatment may be utilized in a wide array of applications to aid or alleviate numerous symptoms or conditions. These applications include the following non-limiting examples: as a liquid band-aid that provides painless removal; as combination product with Manuka honey (see above) to accelerate healing of skin traumas; as "second skin" burn-healing protocol, with anti-microbials added, to speed healing and to protect burns from abrasion and painful air exposure; as a treatment of intact blisters (i.e. the silicone layer may be applied to press blisters down and enable fluids to be reabsorbed; as a treatment/camouflage for cold sores; as a treatment/pain control and camouflage for shingles (Herpes Zoster); as pre-anesthetic procedure or anesthetic application (i.e. as a lidocaine gel/patch for pain control); as sealant on wounds from medical device that pierces skin (i.e. to create a protective layer that prevents contamination, leakage of air);

as post procedure, post injection, application to accelerate bruise healing; similarly, for use in post-laser, post-microneedling applications, post-chemical peel applications, and post-surgical applications; as a general moisture barrier (e.g. a diaper paired with anti-irritation cream); for neck treatments; for earlobe tear prosthesis, after damage from "spacers"; as a treatment for breastfeeding wound/chaffing of nipple (i.e. nipple protectant and possible sheath around outer nipple while breastfeeding); as a treatment for scalp bleeding; as a treatment for dermatitis barrier on fingertips; as a treatment for smoothing smoker's wrinkle lines around lips; as a tattoo covering during healing, with or without possible anti-microbial and/or topical analgesic; as additional protection to more serious wounds (i.e. several silicone layers may be built up around wounds).

A skin treatment and camouflage composition has been described. The foregoing description of the various exemplary embodiments of the invention has been presented for the purposes of illustration and disclosure. It is not intended to be exhaustive or to limit the invention to the precise form disclosed. Many modifications and variations are possible in light of the above teaching without departing from the spirit of the invention.

While the invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and scope of the appended claims.

What is claimed is:

1. A method for treating at least one of a burn, a wound, a scar and a keloid on a user's skin, comprising:
   applying a first silicone-containing elastomer component to the at least one of the burn, the wound, the scar and the keloid on the user's skin, the first silicone-containing elastomer component comprising:
      between 0.03-0.09 wt % of a silicone platinum catalyst;
      between 50-80 wt % of a polydimethylsiloxane;
      between 10-25 wt % of a noncrystalline silicone dioxide; and
      between 0.18-0.49 wt % of a hydroxyl terminated polymethylphenylsiloxane;
   applying a second silicone-containing elastomer component to the at least one of the burn, the wound, the scar and the keloid on the user's skin, the second silicone-containing elastomer component comprising:
      no more than 10 wt % of a crosslinker;
      between 50-80 wt % of a polydimethylsiloxane;
      between 10-25 wt % of a noncrystalline silicone dioxide; and
      between 0.18-0.49 wt % of a hydroxyl terminated polymethylphenylsiloxane;
   mixing the first and second silicone-containing components on the at least one of the burn, the wound, the scar and the keloid on the user's skin to create an elastomer gel that forms, within ten minutes, a film having a thickness and tensile strength effective to compress the user's skin and decrease formation of fibroblasts;
   wherein at least one of the first and second components comprises between 0.49-0.98 wt % of amorphous fumed silica; and
   wherein the film is water resistant, provides a protective layer to the user's skin, and can be peeled off as a single piece.

2. The method of claim 1, wherein applying the first and second silicone-containing elastomer components comprises applying substantially equal volumes of the first and second components.

3. The method of claim 1, wherein the film provides the protective layer to the user's skin for at least two days.

4. The method of claim 1, wherein the thickness and tensile strength of the film is effective to press blisters down.

5. The method of claim 1, wherein the thickness and tensile strength of the film is effective to decrease a biochemical cascade that promotes scar formation.

6. The method of claim 1, further comprising applying a mineral powder to the mixed first and second components, wherein the mineral powder is formulated to decrease cure time of the mixed first and second components.

7. The method of claim 6, wherein the mineral powder comprises fumed silica.

8. The method of claim 1, wherein the first and second components are formulated such that when the first and second components are applied to the user's skin and mixed, the film is formed within 5 minutes.

9. A method for treating a damaged or wounded skin, comprising:
   mixing a first silicone-containing elastomer component with a second silicone-containing elastomer component to create an elastomer gel;
   applying the elastomer gel on the damaged or wounded skin to form a film within ten minutes;
   wherein the first silicone-containing elastomer component comprises:
      between 0.03-0.09 wt % of a silicone platinum catalyst;
      between 50-80 wt % of a polydimethylsiloxane;
      between 10-25 wt % of a noncrystalline silicone dioxide; and
      between 0.18-0.49 wt % of a hydroxyl terminated polymethylphenylsiloxane;
   wherein the second silicone-containing elastomer component comprises:
      no more than 10 wt % of a crosslinker;
      between 50-80 wt % of a polydimethylsiloxane;
      between 10-25 wt % of a noncrystalline silicone dioxide; and
      between 0.18-0.49 wt % of a hydroxyl terminated polymethylphenylsiloxane;
   wherein at least one of the first and second components comprises between 0.49-0.98 wt % of amorphous fumed silica;
   wherein the film has a thickness and tensile strength effective to compress the damaged or wounded skin to decrease formation of fibroblasts; and
   wherein the film is water resistant, provides a protective layer to the user's skin, and can be peeled off as a single piece.

10. The method of claim 9, wherein applying the first and second silicone-containing elastomer components comprises applying substantially equal volumes of the first and second components.

11. The method of claim 9, wherein the film provides the protective layer to the user's skin for at least two days.

12. The method of claim 9, wherein the thickness and tensile strength of the film is effective to press blisters down.

13. The method of claim 9, wherein the thickness and tensile strength of the film is effective to decrease a biochemical cascade that promotes scar formation.

14. The method of claim 9, further comprising applying a mineral powder to the mixed first and second components, wherein the mineral powder is formulated to decrease cure time of the mixed first and second components.

15. The method of claim 14, wherein the mineral powder comprises fumed silica.

16. The method of claim 9, wherein the first and second components are formulated such that when the first and second components are applied to the user's skin and mixed, the film is formed within 5 minutes.

* * * * *